US006262084B1

(12) United States Patent
Biediger et al.

(10) Patent No.: US 6,262,084 B1
(45) Date of Patent: *Jul. 17, 2001

(54) COMPOUNDS THAT INHIBIT THE BINDING OF INTEGRINS TO THEIR RECEPTORS

(75) Inventors: Ronald J. Biediger, Houston; Vanessa O. Grabbe, Sugar Land, both of TX (US); George W. Holland, North Caldwell, NJ (US); Jamal Kassir, Houston; Karin M. Keller, Austin, both of TX (US); Timothy P. Kogan, deceased, late of Escondido, CA (US), by Patricia Woodard Kogan, executrix; Shuqun Lin, Huntingdon Valley, PA (US); Robert V. Market, Pearland, TX (US); Bore G. Raju, Fremont, CA (US); Ian L. Scott, Albany, NY (US); Chengde Wu, Houston, TX (US)

(73) Assignee: Texas Biotechnology Corporation, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/417,886

(22) Filed: Oct. 14, 1999

Related U.S. Application Data

(63) Continuation-in-part of application No. 09/292,459, filed on Apr. 15, 1999, now Pat. No. 6,096,773.
(60) Provisional application No. 60/082,019, filed on Apr. 16, 1998.

(51) Int. Cl.⁷ .................. A61K 31/192; A61K 31/381; C07D 257/04; C07D 317/48; C07D 409/02
(52) U.S. Cl. .................. 514/338; 514/444; 514/512; 546/283.7; 548/267.8; 549/60; 549/452; 562/431
(58) Field of Search .................. 549/60, 452; 562/431; 514/444, 467, 512, 557, 382, 338; 548/252, 267.8; 546/283.7

(56) References Cited

U.S. PATENT DOCUMENTS

| 4,372,974 | 2/1983 | Fish et al. .................. 424/319 |
| 5,192,746 | 3/1993 | Lobl et al. .................. 514/11 |
| 5,510,332 | 4/1996 | Kogan et al. .................. 514/14 |
| 5,654,301 | * 8/1997 | Kohn et al. . |
| 5,770,573 | 6/1998 | Arrhenius et al. . |
| 5,821,231 | 10/1998 | Arrhenius et al. . |
| 5,936,065 | 8/1999 | Arrhenius et al. . |

FOREIGN PATENT DOCUMENTS

| 0 341 915 | 5/1989 | (EP) .................. C07K/5/00 |
| 0 422 937 A1 | 11/1990 | (EP) .................. C07K/15/00 |
| WO 94/22820 | 10/1994 | (WO) . |
| WO 95/15973 | 6/1995 | (WO) .................. C07K/5/08 |
| WO 96/06108 | 2/1996 | (WO) .................. C07K/5/10 |
| WO 96/22966 | 8/1996 | (WO) .................. C07C/237/22 |
| WO 98/04247 | 2/1998 | (WO) .................. A61K/31/00 |
| WO 98/04913 | 2/1998 | (WO) .................. G01N/33/00 |
| 9804247 | * 2/1998 | (WO) . |
| WO 99/06434 | 2/1999 | (WO) . |
| WO 99/24398 | 5/1999 | (WO) . |
| 99/52493 | 10/1999 | (WO) . |
| 99/52898 | 10/1999 | (WO) . |

OTHER PUBLICATIONS

Windholz et al, Eds. The Merck Index, 10th Ed. pp. 1271 (1983).*

* cited by examiner

*Primary Examiner*—Taofiq A. Solola
(74) *Attorney, Agent, or Firm*—Rockey, Milnamow & Katz, Ltd.

(57) ABSTRACT

A method for the inhibition of the binding of $\alpha_4\beta_1$ integrin to its receptors, for example VCAM-1 (vascular cell adhesion molecule-1) and fibronectin; compounds that inhibit this binding; pharmaceutically active compositions thereof; and the use of the compounds either as above, or in formulations for the control or prevention of diseases states in which $\alpha_4\beta_1$ is involved.

10 Claims, No Drawings

COMPOUNDS THAT INHIBIT THE BINDING OF INTEGRINS TO THEIR RECEPTORS

CROSS-REFERENCE TO RELATED APPLICATIONS

This application is a continuation-in-part of U.S. patent application Ser. No. 09/292,459 filed Apr. 15, 1999, now U.S. Pat. No. 6,096,973 which is a continuation-in-part claiming the benefit of U.S. Provisional Application No. 60/082,019, filed Apr. 16, 1998.

FIELD OF THE INVENTION

This invention is directed generally to the inhibition of the binding of $\alpha_4\beta_1$ integrin to its receptors, for example VCAM-1 (vascular cell adhesion molecule-1) and fibronectin. The invention also relates to compounds that inhibit this binding; to pharmaceutically active compositions comprising such compounds; and the use of such compounds either as above, or in formulations for the control or prevention of disease states in which $\alpha_4\beta_1$ is involved.

BACKGROUND OF THE INVENTION

When a tissue has been invaded by a microorganism or has been damaged, white blood cells, also called leukocytes, play a major role in the inflammatory response. One of the most important aspects of the inflammatory response involves the cell adhesion event. Generally, white blood cells are found circulating through the bloodstream. However, when a tissue is infected or becomes damaged, the white blood cells recognize the invaded or damaged tissue, bind to the wall of the capillary and migrate through the capillary into the affected tissue. These events are mediated by a family of proteins called cell adhesion molecules.

There are three main types of white blood cells: granulocytes, monocytes and lymphocytes. The integrin $\alpha_4\beta_1$ (also called VLA-4 for very late antigen-4) is a heterodimeric protein expressed on the surface of monocytes, lymphocytes and two subclasses of granulocytes: eosinophils and basophils. This protein plays a key role in cell adhesion through its ability to recognize and bind VCAM-1 and fibronectin, proteins associated with the endothelial cells that line the interior wall of capillaries.

Following infection or damage of tissue surrounding a capillary, endothelial cells express a series of adhesion molecules, including VCAM-1, that are critical for binding the white blood cells that are necessary for fighting infection. Prior to binding to VCAM-1 or fibronectin, the white blood cells initially bind to certain adhesion molecules to slow their flow and allow the cells to "roll" along the activated endothelium. Monocytes, lymphocytes, basophils and eosinophils are then able to firmly bind to VCAM-1 or fibronectin on the blood vessel wall via the $\alpha_4\beta_1$ integrin. There is evidence that such interactions are also involved in transmigration of these white blood cells into the damaged tissue, as well as the initial rolling event itself.

Although white blood cell migration to the site of injury helps fight infection and destroy foreign material, in many instances this migration can become uncontrolled, with white blood cells flooding to the scene, causing widespread tissue damage. Compounds capable of blocking this process, therefore, may be beneficial as therapeutic agents. Thus, it would be useful to develop inhibitors that would prevent the binding of white blood cells to VCAM-1 and fibronectin.

Some of the diseases that might be treated by the inhibition of $\alpha_4\beta_1$ binding include, but are not limited to, atherosclerosis, rheumatoid arthritis, asthma, allergy, multiple sclerosis, lupus, inflammatory bowel disease, graft rejection, contact hypersensitivity, sickle cell disease and type I diabetes. In addition to being found on some white blood cells and some reticulocytes, $\alpha_4\beta_1$ is also found on various cancer cells, including leukemia, melanoma, lymphoma and sarcoma cells. It has been suggested that cell adhesion involving $\alpha_4\beta_1$ may be involved in the metastasis of certain cancers. Inhibitors of $\alpha_4\beta_1$ binding may, therefore, also be useful in the treatment of some forms of cancer.

The isolation and purification of a peptide which inhibits the binding of $\alpha_4\beta_1$ to a protein is disclosed in U.S. Pat. No. 5,510,332. Peptides which inhibit binding are disclosed in WO 95/15973, EP 0 341 916, EP 0 422 938 A1, U.S. Pat. No. 5,192,746 and WO 96/06108. Novel compounds which are useful for inhibition and prevention of cell adhesion and cell adhesion-mediated pathologies are disclosed in WO 96/22966, WO 98/04247 and WO 98/04913.

It is therefore an object of the invention to provide novel compounds which are inhibitors of $\alpha_4\beta_1$ binding, and pharmaceutical compositions including such novel compounds.

The present invention also relates to pharmaceutical compositions comprising a physiologically acceptable diluent and at least one compound of the present invention.

The present invention further relates to a process of inhibiting the binding of $\alpha_4\beta_1$ integrin to VCAM-1 comprising exposure of a cell expressing $\alpha_4\beta_1$ integrin to a cell expressing VCAM-1 in the presence of an effective inhibiting amount of a compound of the present invention. The VCAM-1 may be on the surface of a vascular endothelial cell, an antigen presenting cell, or other cell type. The $\alpha_4\beta_1$ may be on a white blood cell such as a monocyte, lymphocyte, granulocyte; a stem cell; or any other cell that naturally expresses $\alpha_4\beta_1$.

The invention also provides a method for treating disease states mediated by $\alpha_4\beta_1$ binding which comprises administration of an effective amount of a compound of the present invention, either alone or in formulation, to an afflicted patient.

BRIEF SUMMARY OF THE INVENTION

The invention is directed to novel compounds of Formula I as follows:

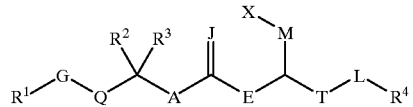

Formula I wherein A is selected from the group consisting of —O—, —S—, and —NR$^5$—;

E is selected from the group consisting of —CH$_2$—, —O—, —S—, and —NR$^6$;

Q is selected from the group consisting of —C(O)— and —(CH$_2$)$_k$— wherein k is an integer of 0 or 1;

J is selected from the group consisting of —O—, —S— and NR$^8$—;

G is selected from the group consisting of —O—, —NH—, —S—, and —(CH$_2$)$_p$— wherein p is an integer of 0 or 1;

T is selected from the group consisting of —C(O)— and —(CH$_2$)$_b$— wherein b is an integer of from 0 to 3;

L is selected from the group consisting of —O—, —NR$^7$—, —S—, and —(CH$_2$)$_n$— wherein n is an integer of 0 or 1;

M is selected from the group consisting of —C(R$^9$)(R$^{10}$)— and —(CH$_2$)$_u$—, wherein u is an integer of from 0 to 3;

X is selected from the group consisting of —CO$_2$B, —PO$_3$H$_2$, —SO$_3$H, —OPO$_3$H$_2$, —C(O)NHC(O)R$^{11}$, —C(O)NHSO$_2$R$^{12}$, oxazolyl, tetrazolyl and hydrogen;

B, R$^1$, R$^2$, R$^3$, R$^4$, R$^5$, R$^6$, R$^7$, R$^8$, R$^9$, R$^{10}$, R$^{11}$, and R$^{12}$ are independently selected from the group consisting of hydrogen, halogen, hydroxyl, alkyl, alkenyl, alkynyl, alkoxy, alkenoxy, alkynoxy, thioalkoxy, aliphatic acyl, —CF$_3$, nitro, amino, cyano, —N(C$_1$–C$_3$ alkyl)—C(O)(C$_1$–C$_3$ alkyl), —C$_1$–C$_3$ alkylamino, alkenylamino, alkynylamino, di(C$_1$–C$_3$ alkyl)amino, —C(O)O—(C$_1$–C$_3$ alkyl), —C(O)NH—(C$_1$–C$_3$ alkyl), —CH=NOH, —PO$_3$H$_2$, —OPO$_3$H$_2$, —C(O)N(C$_1$–C$_3$ alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkenyl, aralkyl, alkylheterocyclyl, heterocyclylalkyl, sulfonyl, sulfonamido, carbamate, aryloxyalkyl, carboxyl and —C(O)NH(benzyl);

wherein B, X, R$^1$, R$^2$, R$^3$, R$^4$, R$^5$, R$^6$, R$^7$, R$^8$, R$^9$, R$^{10}$, R$^{11}$, and R$^{12}$ are unsubstituted or substituted with at least one electron donating or electron withdrawing group;

and wherein R$^2$ and R$^3$ taken together may form a first ring;

R$^4$ and R$^7$ taken together may form a second ring;

R$^9$ and R$^{10}$ taken together may form a third ring;

and pharmaceutically acceptable salts thereof.

For Formula I, presently preferred compounds may have R$^1$, R$^2$ and R$^3$ as hydrogen, alkoxy, alkoxyalkoxy, aryl, alkylaryl, arylalkyl, heterocyclyl, heterocyclylalkyl, alkylheterocyclyl or alkyl; R$^4$ as aryl, alkylaryl, arylalkyl, heterocyclyl, alkylheterocyclyl or heterocyclylalkyl; X as —CO$_2$B; and M as —C(R$^9$)(R$^{10}$)— wherein R$^9$ and R$^{10}$ are hydrogen or lower alkyl.

More specifically, the compounds of the present invention may be described by Formula II below.

Formula II wherein X is selected from the group consisting of —CO$_2$B, —PO$_3$H$_2$, —SO$_3$H, —OPO$_3$H$_2$, —C(O)NHC(O)R$^{11}$, —C(O)NHSO$_2$R$^{12}$, oxazolyl, tetrazolyl and hydrogen; and B, R$^1$, R$^2$, R$^3$, R$^4$, R$^5$, R$^6$, R$^9$, R$^{10}$, R$^{11}$, and R$^{12}$ are independently selected from the group consisting of hydrogen, halogen, hydroxyl, alkyl, alkenyl, alkynyl, alkoxy, alkenoxy, alkynoxy, thioalkoxy, aliphatic acyl, —CF$_3$, nitro, amino, cyano, —N(C$_1$–C$_3$ alkyl)—C(O)(C$_1$–C$_3$ alkyl), —C$_1$–C$_3$ alkylamino, alkenylamino, alkynylamino, di(C$_1$–C$_3$ alkyl)amino, —C(O)O—(C$_1$–C$_3$ alkyl), —C(O)NH—(C$_1$–C$_3$ alkyl), —CH=NOH, —PO$_3$H$_2$, —OPO$_3$H$_2$, —C(O)N(C$_1$–C$_3$ alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkenyl, aralkyl, alkylheterocyclyl, heterocyclylalkyl, sulfonyl, sulfonamido, carbamate, aryloxyalkyl, carboxyl and —C(O)NH(benzyl);

B, X, R$^1$, R$^2$, R$^3$, R$^4$, R$^5$, R$^6$, R$^9$, R$^{10}$, R$^{11}$ and R$^{12}$ and are unsubstituted or substituted with at least one electron donating or electron withdrawing group.

For Formula II, presently preferred compounds may have R$^1$, R$^2$ and R$^3$ as independently hydrogen, alkoxy, alkoxyalkoxy, aryl, alkylaryl, arylalkyl, heterocyclyl, alkylheterocyclyl, heterocyclylalkyl or alkyl; R$^4$ as aryl, alkylaryl, arylalkyl, heterocyclyl, heterocyclylalkyl or alkyheterocyclyl; R$^5$ and R$^6$ as hydrogen; and R$^9$ and R$^{10}$ are independently hydrogen or lower alkyl.

Presently preferred compounds are (3S)-3-(1,3-benzodioxol-5-yl)-3-([[((1S)-1-[(2-thienylmethyl)amino]carbonylpentyl)amino]carbonylamino)propanoic acid, (3S)-3-(1,3-benzodioxol-5-yl)-3-([[((1S)-1-[(2-acetylphenyl)amino]carbonylpentyl)amino]carbonylamino)propanoic acid, (3S)-3-(1,3-benzodioxol-5-yl)-3-([[((1S)-1-[(4-acetylphenyl)amino]carbonylpentyl)amino]carbonylamino)propanoic acid, 3-(3S)-3-(1,3-benzodioxol-5-yl)-3-([[((1S)-1-[(4-(2-thienylmethyl)aminobenzyl)amino]carbonylpentyl)amino]carbonylamino)propanoic acid, 3-(3S)-3-(1,3-benzodioxol-5-yl)-3-([[((1S)-1-[(4-(2-methylbenzyloxy)-3-methoxybenzyl)amino]carbonylpentyl)amino]carbonylamino)propanoic acid, 3(3S)-3-(1,3-benzodioxol-5-yl)-3-([[((1S)-1-[(4-(2-methylbenzyl)amino)benzyl)amino]carbonylpentyl)amino]carbonylamino)propanoic acid, 3(3S)-3-(1,3-benzodioxol-5-yl)-3-([[((1S)-1-[(4-(1,3-thiazol-2-ylmethyl)aminobenzyl)amino]carbonylpentyl)amino]carbonylamino)propanoic acid, 3(3S)-3-(1,3-benzodioxol-5-yl)-3-([[((1S)-1-[(4-(5-methyl-2-thienylmethyl)aminobenzyl)amino]carbonylpentyl)amino]carbonylamino)propanoic acid, 3(3S)-3-(1,3-benzodioxol-5-yl)-3-([[((1S)-1-[(4-(2-thienylsulfonamido)benzyl)amino]carbonylpentyl)amino]carbonylamino)propanoic acid, 3(3S)-3-(1,3-benzodioxol-5-yl)-3-([[((1S)-1-[(4-(2-(6-methylpyridyl)methyl)benzyl)amino]carbonylpentyl)amino]carbonyl amino)propanoic acid, (3S)-3-(1,3-benzodioxol-5-yl)-3-(((((1S)-3-(methylsulfanyl)-1-((phenylsulfanyl)methyl)propyl)amino)carbonyl)amino)propanoic acid, (3S)-3-(1,3-benzodioxol-5-yl)-3-(((((1S)-2-((cyclopropylmethyl)thio)-1-((phenylthio)methyl)ethyl)amino)carbonyl)amino)propanoic acid, (9S, 13S)-1,3-(1,3-benzodioxol-5-yl)-3,11-dioxo-1-phenyl-9-{[(2-thienylmethyl)amino]carbonyl}-2-oxa-4,10,12-triazapentadecan-15-oic acid, (9S,13S)-13-(1,3-benzodioxol-5-yl)-9-{[(3-hydroxy-4-methoxybenzyl)amino]carbonyl}- 3,11-dioxo-2-oxa-4,10,12-triazapentadecan-15-oic acid, (3S)-3-(1,3-benzodioxol-5-yl)-3-{[({(1S)-2-(benzylsulfanyl)-1-[(phenylsulfanyl)methyl]ethyl}amino)carbonyl]amino}propanoic acid, (3S)-3-(1,3-benzodioxol-5-yl)-3-{[({(1S)-3-(methylsulfanyl)-1-[({4-[(2-toluidinocarbonyl)amino]phenyl}sulfanyl)methyl]propyl}amino)carbonyl]amino}propanoic acid, (3S)-3-(1,3-benzodioxol-5-yl)-3-{[({(1S)-2-(ethylsulfanyl)-1-[(phenylsulfanyl)methyl]ethyl}amino)carbonyl]amino}propanoic acid, (9S,13S)-13-(1,3-benzodioxol-5-yl)-9-[({4-[(2-methylbenzyl)amino]benzyl}amino)carbonyl]-3,11-dioxo-1-phenyl-2-oxa-4,10,12-triazapentadecan-15-oic acid, (3S)-3-(1,3-benzodioxol-5-yl)-3-{[({(1S)-3-(methylsulfanyl)-1-[({3-[(2-toluidinocarbonyl)amino]phenyl}sulfanyl)methyl]propyl}amino)carbonyl]amino}propanoic acid, (3S)-3-(1,3-benzodioxol-5-yl)-3-{[({(1S)-2-(ethylthio)-1-[(phenylthio)methyl]ethyl}oxy)carbonyl]amino}propanoic acid, (9S, 13S)-13-(1,3- benzodioxol-5-yl)-3,11-dioxo-1-phenyl-9-(((4-((2-toluidinocarbonyl)amino)benzyl)amino)carbonyl)-2-oxa-4,10,12-triazapentadecan-15-oic acid, or pharmaceutically acceptable salts thereof.

Derivatives of Formulas I, and II include esters, carbamates, aminals, amides, optical isomers and pro-drugs.

The present invention also relates to pharmaceutical compositions comprising a physiologically acceptable diluent and at least one compound of the present invention.

The present invention further relates to a process of inhibiting the binding of $\alpha_4\beta_1$ integrin to VCAM-1 comprising exposure of a cell expressing $\alpha_4\beta_1$ integrin to a cell expressing VCAM-1 in the presence of an effective inhibiting amount of a compound of the present invention. The VCAM-1 may be on the surface of a vascular endothelial cell, an antigen presenting cell, or other cell type. The $\alpha_4\beta_1$ may be on a white blood cell such as a monocyte, lymphocyte, granulocyte; a stem cell; or any other cell that naturally expresses $\alpha_4\beta_1$.

The invention also provides a method for treating disease states mediated by $\alpha_4\beta_1$ binding which comprises administration of an effective amount of a compound of the present invention, either alone or in formulation, to an afflicted patient.

DETAILED DESCRIPTION OF THE INVENTION

Definitions of Terms

The term "alkyl" as used herein alone or in combination refers to $C_1$–$C_{12}$ straight or branched, substituted or unsubstituted saturated chain radicals derived from saturated hydrocarbons by the removal of one hydrogen atom. Representative examples of alkyl groups include methyl, ethyl, n-propyl, iso-propyl, n-butyl, sec-butyl, iso-butyl, and tert-butyl among others.

The term "alkenyl", alone or in combination, refers to a substituted or unsubstituted straight-chain or substituted or unsubstituted branched-chain alkenyl radical containing from 2 to 10 carbon atoms. Examples of such radicals include, but are not limited to, ethenyl, E- and Z-pentenyl, decenyl and the like.

The term "alkynyl", alone or in combination, refers to a substituted or unsubstituted straight or substituted or unsubstituted branched chain alkynyl radical containing from 2 to 10 carbon atoms. Examples of such radicals include, but are not limited to ethynyl, propynyl, propargyl, butynyl, hexynyl, decynyl and the like.

The term "lower" modifying "alkyl", "alkenyl", "alkynyl" or "alkoxy" refers to a $C_1$–$C_6$ unit for a particular functionality. For example lower alkyl means $C_1$–$C_6$ alkyl.

The term "cycloalkyl" as used herein alone or in combination refers to a substituted or unsubstituted aliphatic ring system having 3 to 10 carbon atoms and 1 to 3 rings, including, but not limited to cyclopropyl, cyclopentyl, cyclohexyl, norbornyl, and adamantyl among others. Cycloalkyl groups can be unsubstituted or substituted with one, two or three substituents independently selected from lower alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide. This term is meant to encompass cycloalkenyl and cycloalkynyl groups. "Cycloalkyl" includes cis or trans forms. Furthermore, the substituents may either be in endo or exo positions in the bridged bicyclic systems.

The term "cycloalkenyl" as used herein alone or in combination refers to a cyclic carbocycle containing from 4 to 8 carbon atoms and one or more double bonds. Examples of such cycloalkenyl radicals include, but are not limited to, cyclopentenyl, cyclohexenyl, cyclopentadienyl and the like.

The term "cycloalkylalkyl" as used herein refers to a cycloalkyl group appended to a lower alkyl radical, including, but not limited to cyclohexyl methyl.

The term "halo" or "halogen" as used herein refers to I, Br, Cl or F.

The term "haloalkyl" as used herein refers to a lower alkyl radical, to which is appended at least one halogen substituent, for example chloromethyl, fluoroethyl, trifluoromethyl and pentafluoroethyl among others.

The term "alkoxy", alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkenoxy", alone or in combination, refers to a radical of formula alkenyl-O—, provided that the radical is not an enol ether, wherein the term "alkenyl" is as defined above. Examples of suitable alkenoxy radicals include, but are not limited to, allyloxy, E- and Z-3-methyl-2-propenoxy and the like.

The term "alkynoxy", alone or in combination, refers to a radical of formula alkynyl-O—, provided that the radical is not an -ynol ether. Examples of suitable alkynoxy radicals include, but are not limited to, propargyloxy, 2-butynyloxy and the like.

The term "carboxyl" as used herein refers to —$CO_2H$.

The term "thioalkoxy", refers to a thioether radical of formula alkyl-S—, wherein "alkyl" is as defined above.

The term "carboxaldehyde" as used herein refers to —C(O)R wherein R is hydrogen.

The term "carboxamide" as used herein refers to —C(O)NR$_2$ wherein R is hydrogen, alkyl or any other suitable substituent.

The term "alkoxyalkoxy" as used herein refers to $R_bO$—$R_cO$— wherein $R_b$ is lower alkyl as defined above and $R_c$ is alkylene wherein alkylene is —(CH$_2$)$_{n'}$— wherein n' is an integer from 1 to 6. Representative examples of alkoxyalkoxy groups include methoxymethoxy, ethoxymethoxy, and t-butoxymethoxy among others.

The term "alkylamino" as used herein refers to $R_d$NH— wherein $R_d$ is a lower alkyl group, for example, ethylamino, butylamino, among others.

The term "alkenylamino" alone or in combination, refers to a radical of formula alkenyl-NH— or (alkenyl)$_2$N—, wherein the term "alkenyl" is as defined above, provided that the radical is not an enamine. An example of such alkenylamino radical is the allylamino radical.

The term "alkynylamino", alone or in combination, refers to a radical of formula alkynyl-NH— or (alkynyl)$_2$N— wherein the term "alkynyl" is as defined above, provided that the radical is not an amine. An example of such alkynylamino radicals is the propargyl amino radical.

The term "dialkylamino" as used herein refers to $R_eR_fN$— wherein $R_e$ and $R_f$ are independently selected from lower alkyl, for example diethylamino, and methyl propylamino, among others.

The term "amino" as used herein refers to $H_2N$—.

The term "alkoxycarbonyl" as used herein refers to an alkoxyl group as previously defined appended to the parent molecular moiety through a carbonyl group. Examples of alkoxycarbonyl include methoxycarbonyl, ethoxycarbonyl, and isopropoxycarbonyl among others.

The term "aryl" or "aromatic" as used herein alone or in combination refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group selected from the group consisting of furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl and the like. "Arylalkyl" and "alkylaryl" employ the term "alkyl" as defined above. Rings may be multiply substituted.

The term "aralkyl", alone or in combination, refers to an aryl substituted alkyl radical, wherein the terms "alkyl" and "aryl" are as defined above. Examples of suitable aralkyl radicals include, but are not limited to, phenylmethyl, phenethyl, phenylhexyl, diphenylmethyl, pyridylmethyl, tetrazolyl methyl, furylmethyl, imidazolyl methyl, indolylmethyl, thienylpropyl and the like.

The term "aralkenyl", alone or in combination, refers to an aryl substituted alkenyl radical, wherein the terrns "aryl" and "alkenyl" are as defined above.

The term "arylamino", alone or in combination, refers to a radical of formula aryl-NH—, wherein "aryl" is as defined above. Examples of arylamino radicals include, but are not limited to, phenylamino(anilido), naphthlamino, 2-, 3-, and 4-pyridylamino and the like.

The term "biaryl", alone or in combination, refers to a radical of formula aryl-aryl, wherein the term "aryl" is as defined above.

The term "thioaryl", alone or in combination, refers to a radical of formula aryl-S—, wherein the term "aryl" is as defined above. An example of a thioaryl radical is the thiophenyl radical.

The term "aroyl", alone or in combination, refers to a radical of formula aryl-CO—, wherein the term "aryl" is as defined above. Examples of suitable aromatic acyl radicals include, but are not limited to, benzoyl, 4-halobenzoyl, 4-carboxybenzoyl, naphthoyl, pyridylcarbonyl and the like.

The termn "heterocyclyl", alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxy, carboalkoxy, carboxyalkyl, oxo, arylsulfonyl and aralkylaminocarbonyl among others.

The term "alkylheterocyclyl" as used herein refers to an alkyl group as previously defined appended to the parent molecular moiety through a heterocyclyl group.

The term "heterocyclylalkyl" as used herein refers to a heterocyclyl group as previously defined appended to the parent molecular moiety through an alkyl group.

The term "aminal" as used herein refers to a hemi-acetal of the structure RCH(NH$_2$)(OH).

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed in *Advanced Organic Chemistry* by J. March, 1985, pp. 16–18, incorporated herein by reference. Electron withdrawing groups include halo, nitro, carboxyl, lower alkenyl, lower alkynyl, carboxaldehyde, carboxyamido, aryl, quaternary ammonium, trifluoromethyl, and aryl lower alkanoyl among others. Electron donating groups include such groups as hydroxy, lower alkyl, amino, lower alkylamino, di(lower alkyl)amino, aryloxy, mercapto, lower alkylthio, lower alkylmercapto, and disulfide among others. One skilled in the art will appreciate that the aforesaid substituents may have electron donating or electron withdrawing properties under different chemical conditions. Moreover, the present invention contemplates any combination of substituents selected from the above-identified groups.

The most preferred electron donating or electron withdrawing substituents are halo, nitro, alkanoyl, carboxaldehyde, arylalkanoyl, aryloxy, carboxyl, carboxamide, cyano, sulfonyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkyl)amino, amine lower alkyl mercapto, mercaptoalkyl, alkylthio and alkyldithio.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1–3 atoms containing any combination of —C—, —C(O)—, —NH—, —S—, —S(O)—, —O—, —C(O)O— or —S(O) O—. Rings may be substituted multiple times.

The term "mammals" includes humans and other animals.

The term "heteroatom" as used herein encompasses nitrogen, sulfur and oxygen.

The term "alpha" as used herein indicates the position immediately adjacent to the position described.

For example, R$^1$ in Formulas I and II above may independently be, but are not limited to, phenyl, isobutyl, n-butyl, 2-thienylmethyl, 1,3-thiazol-2-yl-methyl, benzyl, thienyl, 3-pyridinylmethyl, 3-methyl-1-benzothiophen-2-yl, allyl, isobutyl, 3-methoxybenzyl, propyl, 2-ethoxyethyl, cyclopropylmethyl, 4-((2-toluidinocarbonyl)amino)benzyl, 2-pyridinylethyl, 2-(1H-indol-3-yl)ethyl, 1H-benzimidazol-2-yl, 4-piperidinylmethyl, 3-hydroxy-4-methoxybenzyl, 4-hydroxyphenethyl, 4-aminobenzyl, phenylsulfonylmethyl, isopropyl or 2-oxo-1-pyrrolidinyl.

Some of the substituents which may be linked to form a first, second or third ring as described above. Examples of such rings include 4-(2-thienylmethyl)piperazino, 4-(3-thienylmethyl)piperazino, 4-(2-methoxyphenyl)piperazino, 4-(2-thienylcarbonyl)piperazino, 4-(2-thienylsulfonyl) piperazino, 4-((benzyloxy)carbonyl)piperazino, cyclopropyl, cyclobutyl, cyclopentyl, cyclohexyl, 4-piperidinyl, and 4-tetrahydropyranyl, pyrrolidino, 1-piperidino, 4-methyl-1-piperazino, 4-aceto-1-piperazino, or 4-morpholino among others. Rings so formed may be substituted by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, acyloxy, alkoxyalkoxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1–3 atoms containing any combination of —C—, —C(O)—, —NH—, —S—, —S(O)—, —O—, —C(O)O— or —S(O)O—. Rings may be substituted multiple times.

The $R^4$ substituent for Formulas I and II above may be, but is not limited to, 1,3-benzodioxol-5-yl, 1-naphthyl, thienyl, 4-isobutoxyphenyl, 2,6-dimethylphenyl, allyloxyphenyl, 3-bromo-4-methoxyphenyl, 4-butoxyphenyl, 1-benzofuran-2-yl, 2-thienylmethyl, phenyl, methysulfanyl, phenylsulfanyl, phenethylsulfanyl, 4-bromo-2-thienyl, 3-methyl-2-thienyl, or 4,5-dihydro-1,3-oxazol-2-yl. These substituents may be further substituted with groups such as alcohols, ethers, esters, amides, sulfones, sulfides, hydroxyl, nitro, cyano, carboxy, amines, heteroatoms, lower alkyl, lower alkoxy, lower alkoxycarbonyl, acyloxy, alkoxyalkoxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1–3 atoms containing any combination of —C—, —C(O)—, —NH—, —S—, —S(O)—, —O—, —C(O)O— or —S(O)O—. Rings may be substituted multiple times.

Abbreviations

Abbreviations which have been used in the schemes and the examples which follow are: BOC for t-butyloxycarbonyl; EtOAc for ethyl acetate; DMF for dimethylformamide; THF for tetrahydrofuran; Tos for p-toluenesulfonyl; DCC for dicyclohexylcarbodiimide; HOBT for 1-hydroxybenzotriazole; TFAA for trifluoroacetic anhydride; NMM for N-methyl morpholine; DIPEA for diisopropylethylamine; DCM for methylene dichloride; LHMDS for lithium hexamethyl disilazide; NaHMDS for sodium hexamethyl disilazide; CDI for 1,1'-carbonyldiimidazole and TBS for TRIS-buffered saline.

The compound and processes of the present invention will be better understood in connection with the following synthetic schemes which illustrate the methods by which the compounds of the invention may be prepared.

An example of a procedure that may be used to synthesize compounds of the formulae shown above is presented in Scheme 1.

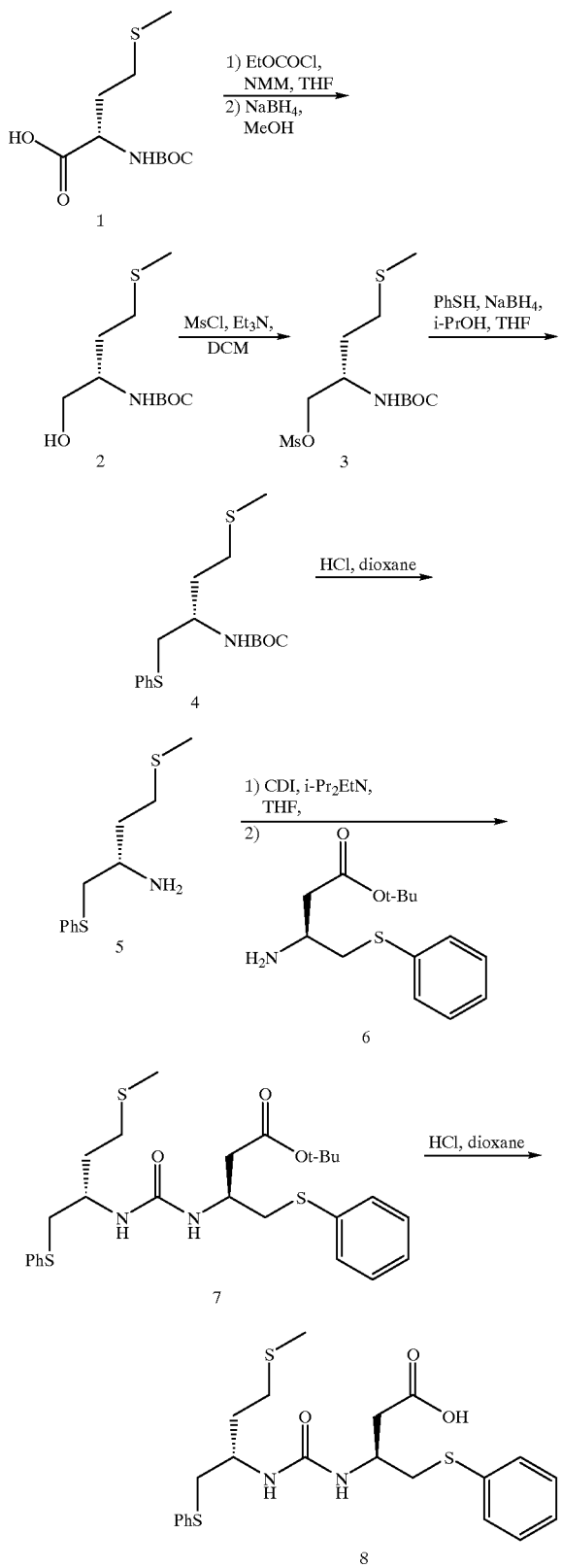

A second example is found in Scheme 2 below.
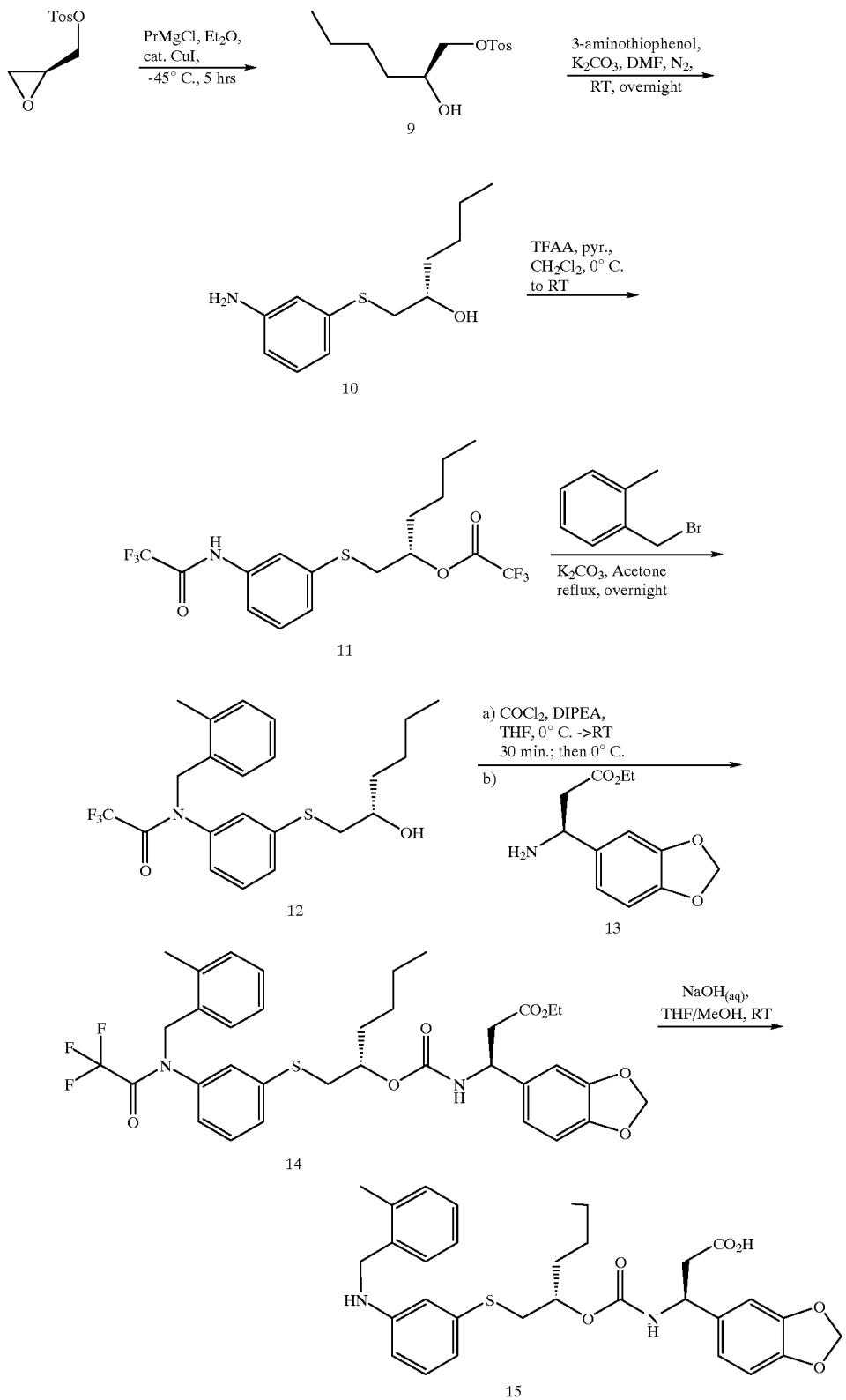
Scheme 2

A third example is found in Scheme 3 below.
Scheme 3
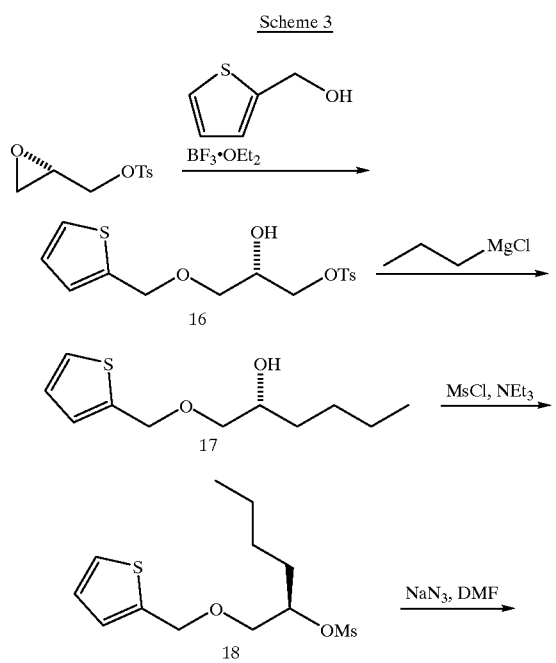
-continued
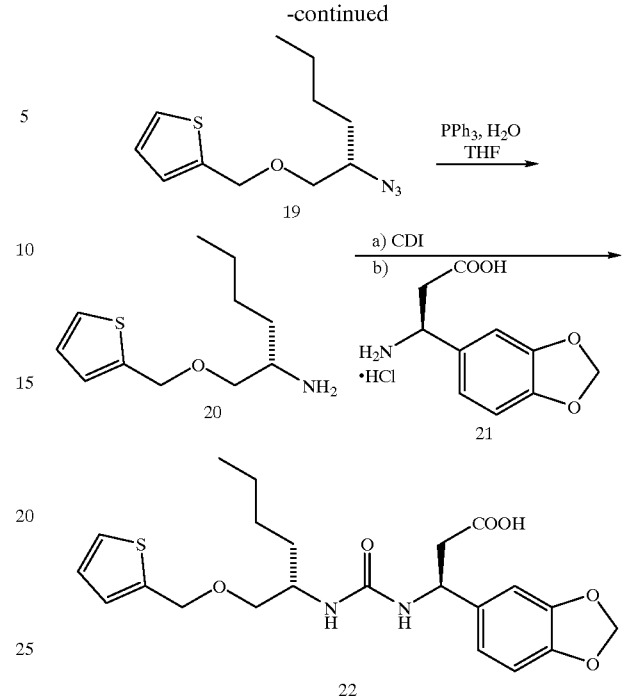
A fourth example is found in Scheme 4 below.
Scheme 4
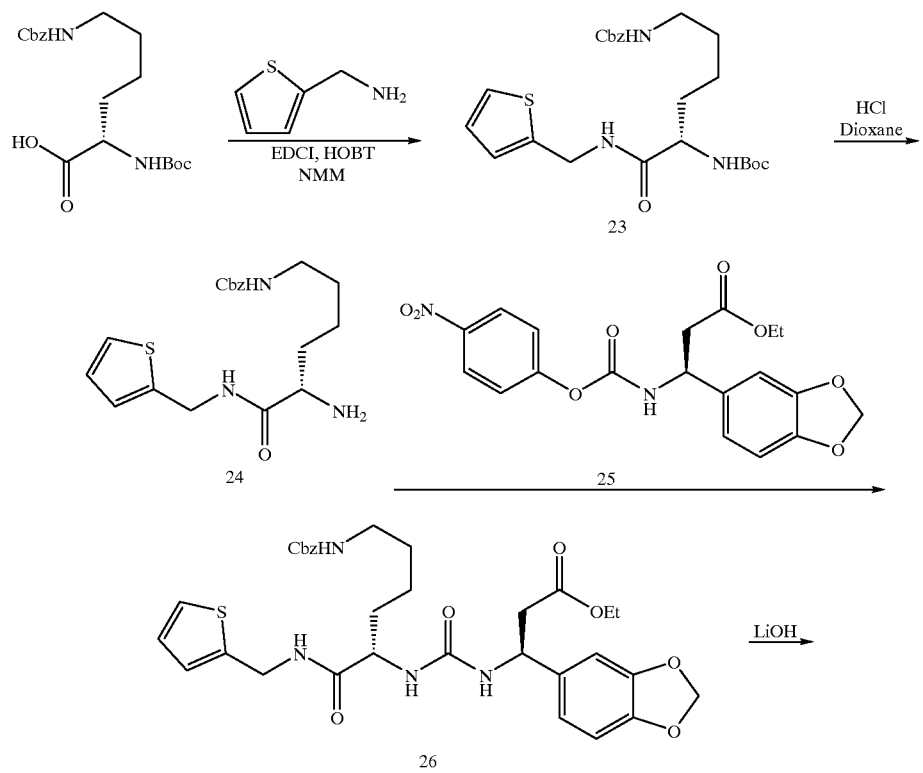

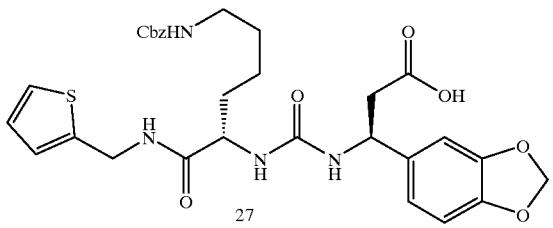

27

A detailed description of the preparation of representative compounds of the present invention is set forth in the Examples.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracistemally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, or the like.

The compositions can also be delivered through a catheter for local delivery at a target site, via an intracoronary stent (a tubular device composed of a fine wire mesh), or via a biodegragable polymer. The compounds may also be complexed to ligands, such as antibodies, for targeted delivery.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Proper fluidity can be maintained, for example, by the use of coating materials such as lecithin, by the maintenance of the required particle size in the case of dispersions and by the use of surfactants.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microeneapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

The present invention contemplates both synthetic compounds of formulas I and II of the present invention, as well as compounds formed by in vivo conversion to compounds of the present invention.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

In another aspect, the present invention contemplates a process of inhibiting the binding of $\alpha_4\beta_1$ integrin to VCAM-1. A process of the present invention can be used either in vitro or in vivo. In accordance with a process of the present invention, a cell expressing $\alpha_4\beta_1$ integrin is exposed to a cell expressing VCAM-1 in the presence of an effective inhibiting amount of a compound of the present invention.

A cell expressing $\alpha_4\beta_1$ integrin can be a naturally occurring white blood cell, mast cell or other cell type that naturally expresses $\alpha_4\beta_1$ on the cell surface, or a cell transfected with an expression vector that contains a polynucleotide (e.g., genomic DNA or cDNA) that encodes $\alpha_4\beta_1$ integrin. In an especially preferred embodiment, $\alpha_4\beta_1$ integrin is present on the surface of a white blood cell such as a monocyte, a lymphocyte or a granulocyte (e.g., an eosinophil or a basophil).

A cell that expresses VCAM-1 can be a naturally occurring cell (e.g. an endothelial cell) or a cell transfected with an expression vector containing a polynucleotide that encodes VCAM-1. Methods for producing transfected cells that express VCAM-1 are well known in the art.

Where VCAM-1 exists on the surface of cell, the expression of that VCAM-1 is preferably induced by inflammatory cytokines such as tumor necrosis factor-$\alpha$, interleukin-4 and interleukin-1$\beta$.

Where the cells expressing $\alpha_4\beta_1$ integrin and VCAM-1 are in a living organism, a compound of the present invention is administered in an effective amount to the living organism. Preferably, the compound is in a pharmaceutical composition of this invention. A process of the present invention is especially useful in treating diseases associated with uncontrolled migration of white blood cells to damaged tissue. Such diseases include, but are not limited to, asthra, atherosclerosis, rheumatoid arthritis, allergy, multiple sclerosis, lupus, inflammatory bowel disease, graft rejection, contact hypersensitivity, type I diabetes, leukemia, and brain cancer. Administration is preferably accomplished via intravascular, subcutaneous, intranasal, transdermal or oral delivery.

The present invention also provides a process of selectively inhibiting the binding of $\alpha_4\beta_1$ integrin to a protein comprising exposing the integrin to the protein in the presence of an effective inhibiting amount of a compound of the present invention. In a preferred embodiment, the $\alpha_4\beta_1$ integrin is expressed on the surface of a cell, either naturally occurring or a cell transformed to express $\alpha_4\beta_1$ integrin.

The protein to which the $\alpha_4\beta_1$ integrin binds can be expressed either on a cell surface or be part of the extracellular matrix. Especially preferred proteins are fibronectin or invasin.

The ability of compounds of the present invention to inhibit binding is described in detail hereinafter in the Examples. These Examples are presented to describe preferred embodiments and utilities of the invention and are not meant to limit the invention unless otherwise stated in the claims appended hereto.

EXAMPLE 1

Synthesis of (3S)-3-{[({(1S)-3-(methylsulfanyl)-1-[(phenylsulfanyl)methyl]propyl)amino)carbonyl]amino}-4-(phenylsulfanyl)butanoic acid (8)

Step One:

N-Boc-L-Methionine 1 (2 g, 8 mmol) was dissolved in THF (40 ML) and the solution cooled to 0° C. N-Methylmorpholine (0.77 mL, 8 mmol) and ethyl chloroformate (0.88 ml, 8 mmol) were added and the mixture was stirred for 30 minutes while maintaining the low temperature. The mixture was quickly filtered and sodium borohydride (0.88 g, 23 mmol) was added. Methanol (100 mL) was added slowly to the ice-cold solution. The ice-bath was removed and the solution stirred at room temperature for 1 hour. A standard aqueous work-up gave the primary alcohol 2 (1.8 g, 95%).

Step Two:

To an ice-cold solution of the alcohol 2 (1.8 g, 7.7 mmol) in methylene chloride (30 mL) was added triethylamine (1.6 mL, 11.5 mmol) and methanesulfonyl chloride (0.8 mL, 10.4 mmol). After 5 minutes, the reaction was poured into water. A standard aqueous work-up gave the mesylate 3 (2.24 g, 93%).

Step Three:

To a solution of the mesylate 3 (1 g, 3.2 mmol) in a mixture of THF (10 mL) and isopropanol (10 ml) was added thiophenol (0.33 mL, 3.2 mmol) and sodium borohydride (0.15 g, 3.9 mmol). The mixture was stirred at room temperature overnight. A standard aqueous work-up gave the sulfide 4 (0.94 g, 90%).

Step Four:

To a solution of the sulfide 4 (0.94 g, 2.9 mmol) in 1,4-dioxane (3 mL) was added hydrochloric acid (3 mL, 4M: 1,4-dioxane) and the solution was stirred at room temperature for 4 hours. Nitrogen was bubbled through the solution to drive off most of the excess HCl. Concentration under reduced pressure, followed by high vacuum, gave the amine hydrochloride 5 (0.86 g). The excess weight was due to residual 1,4-dioxane.

Step Five:

A solution of the amine hydrochloride 5 (0.21 g, 0.8 mmol), and carbonyldiimidazole (0.15 g, 0.9 mmol) in methylene chloride (2 mL) was stirred at room temperature for 30 minutes. A solution of the amine 6 (prepared from Boc-L-Asp(OtBu)-OH following the above reaction sequence) (0.266 g, 0.9 mmol) in methylene chloride (1 mL) was added and the mixture was stirred first at room temperature overnight and then at 40° C. for 1 hour. A standard acid-base work-up, followed by purification by flash chromatography (silica: eluent 3:1–2:1 hexanes:ethyl acetate) gave the urea 7 (0.427 g, quant.).

Step Six:

To a solution of the urea 7 (0.328 g, 0.6 mmol) in 1,4-dioxane (1 mL) was added hydrochloric acid (1 mL, 4M: 1,4-dioxane) and the solution was stirred at room temperature overnight. A standard aqueous work-up, followed by flash chromatography (silica:chloroform—9:1 chloroform:methanol) gave the title compound 8 (0.065 g, 37%). $^1$H NMR: (400 MHz: DMSO-$d_6$) δ 1.63 (1H, m), 1.88 (1H, m), 2.01 (3H, s), 2.35–2.60 (4H, m), 2.97 (1H, dd), 3.06 (1H, dd), 3.12 (1H, dd), 3.17 (1H, dd), 3.82 (1H, m), 4.06 (1H, br ddd), 6.01 (1H, d, NH), 6.14 (1H, d, NH), 7.17 (2H, m), 7.30 (4H, m), 7.38 (4H, m).

EXAMPLE 2

Synthesis of (3S)-3-(1,3-benzodioxol-5-yl)-3-{[({(1S)-1-[({3-[(2-methylbenzyl)amino]phenyl}thio)methyl]pentyl}oxy)carbonyl]amino}propanoic acid (15)

Step One:

Copper (I) iodide (0.63 g, 3.3 mmol) was suspended in diethyl ether (100 mL) and chilled to −45° C. under nitrogen. n-Propylmagnesium chloride (16 mL, 1.0 M in diethyl ether, 16.0 mmol) was added slowly to the solution. After 10 minutes, (2S)-(+)-glycidyl tosylate (5.00 g, 21.9 mmol) in diethyl ether (100 mL) was added dropwise via cannula over 1 hour. After 5 hours, the mixture was warmed to 0° C. and quenched with saturated, aqueous ammonium chloride (50 mL). The mixture was diluted with water and extracted with ethyl acetate. The organic layer was washed with water and brine. The organic layer was dried over $Na_2SO_4$, filtered, and concentrated under reduced pressure. Compound 9 (5.61 g, 90%) was recovered as a clear oil and was used without further purification.

Step Two:

Compound 9 (1.55 g, 5.7 mmol) was dissolved in DMF (20.5 mL) at room temperature. Potassium carbonate (1.07 g, 7.7 mmol) was added and the suspension was sparged with nitrogen gas for 15 minutes. 3-Aminothiophenol (0.60 mL, 5.7 mmol) was introduced via syringe and the solution was stirred overnight. The mixture was diluted with water and ethyl acetate, and the pH of the aqueous layer was adjusted with dilute HCl to pH 5–6. The organic layer was washed with water and brine. The organic solution was dried over $Na_2SO_4$, filtered, and concentrated under reduced pressure. Compound 10 (1.25 g, 98%) was recovered as a yellow oil and was used without further purification.

Step Three:

Compound 10 (1.25 g, 5.7 mmol) and pyridine (1.3 mL, 15.9 mmol) were dissolved in dichloromethane (23.5 mL) and chilled to 0° C. The solution was treated with trifluoroacetic anhydride (2.0 mL, 14.1 mmol) and allowed to warm to room temperature overnight. The mixture was washed with 2N HCl, water and brine. The organic layer was dried over $Na_2SO_4$, filtered, and concentrated under reduced pressure. Compound 11 (2.05 g, 92%) was recovered as a yellow oil and was used without further purification.

Step Four:

Compound 11 (0.52 g, 1.25 mmol) was dissolved in acetone (5.5 mL). The resulting solution was treated with potassium carbonate and α-bromo-o-xylene (0.40 mL, 3.0 mmol) and refluxed overnight. The mixture was cooled and concentrated under reduced pressure. Purification by chromatography (silica gel, 4:1 hexanes:ethyl acetate) gave 12 (0.36g, 69%).

Step Five:

Compound 12 (0.20 g, 0.51 mmol) was dissolved in THF (1.0 mL) and N,N-diisopropylethylamine (0.107 mL, 0.61 mmol) was added. The reaction mixture was chilled to 0° C. under nitrogen, and phosgene (0.32 mL, 20% in toluene) was added via syringe. The mixture was stirred 30 minutes at 0° C., then 2 hours at room temperature and then was recooled to 0° C. A solution of ethyl 3-amino-3-(3,4-methylenedioxyphenyl)propionate (13) (0.13 g, 0.56 mmol) and N,N-diisopropylethylamine (0.107 mL, 0.61 mmol) in THF (1.0 mL) was added by dropwise via cannula. The mixture was warmed to room temperature and stirred an additional 1 hour. The mixture was diluted with ethyl acetate and washed with 2N HCl, water and brine. The organic layer was dried over $Na_2SO_4$, filtered, and concentrated under reduced pressure. Purification by chromatography (silica gel, gradient elution 6:1 to 4:1 hexanes:ethyl acetate) gave 14 (0.19 g, 58%).

Step Six:

Compound 14 (0.19 g, 0.29 mmol) was dissolved in 3:1 THF/water (1.1 mL) and treated with 2N $NaOH_{(aq)}$ (0.3 mL, 0.6 mmol) and methanol (0.3 mL). After 1 hour at room temperature, the mixture was diluted with water and washed with dichloromethane. The ethyl acetate layer was acidified with excess 2N HCl and washed with ethyl acetate (2×). The organic layers were combined, washed with brine and dried over $Na_2SO_4$. The organic solution was filtered and concentrated under reduced pressure to give compound 15 (0.15 g, 94%). $^1$H NMR (400 MHz, DMSO-$d_6$): δ 7.62 (d, J=7.7 Hz, 1H), 7.26 (dd, 1H), 7.14 (m, 4H), 6.99 (dd, J=7.9 Hz, 1H), 6.87 (d, J=1.5 Hz, 1H), 6.79 (d, J=8.0 Hz 1H), 6.75 (dd, J=1.5, 8.0 Hz, 1H), 6.58 (br s, 1H), 6.53 (br d, J=7.3 Hz, 1H), 6.44 (br d, J=8.0 Hz, 1H), 5.96 (s, 2H), 4.83 (dd, J=8.0, 15.4 Hz, 1H), 4.67 (m, 1H), 4.21 (s, 2H), 3.0 (m, 2H), 2.63 (dd, J=8.3, 15.6 Hz, 1H), 2.56 (dd, J=6.6, 15.4 Hz 1H), 2.32 (s, 3H), 1.61 (m, 1H), 1.49 (m, 1H), 1.18 (m 4H), 0.78 (br, s, 3H).

EXAMPLE 3

Synthesis of (3S)-3-(1,3-benzodioxol-5-yl)-3-{[({(1S)-1-[(2-thienylmethoxy)methyl]pentyl}amino)carbonyl]amino}propanoic acid (22).

Step One:

To a solution of (S)-glycidyl tosylate (842 mg, 3.69 mmol) and 2-thiophenemethanol (842 mg, 7.38 mmol) in $CH_2Cl_2$ (7.4 ml) cooled to 0° C. under a dry nitrogen atmosphere, $BF_3$ $OEt_2$ (0.046 ml, 0.37 mmol) was added by syringe. The mixture was warmed to room temperature and stirred 4 days, then concentrated under reduced pressure. The residue was purified by silica gel chromatography, eluting with 3:2 hexanes:ethyl acetate increasing to 1:1 hexanes:ethyl acetate to yield a 2:1 mixture of 16:(S)-glycidyl tosylate (394 mg) as a light yellow oil.

Step Two:

To a solution of a 2:1 mixture of 16:(S)-glycidyl tosylate (320 mg, assume 0.73 mmol 16 and 0.37 mmol (S)-glycidyl tosylate) in diethyl ether (22 ml) cooled to −78° C. under a dry nitrogen atmosphere, propylmagnesiumchloride (2.75 ml of a 2.0 M solution in diethyl ether, 5.5 mmol) was added dropwise by syringe. The resulting mixture was stirred at −78° C. for 15 minutes, then was allowed to warm to room temperature, stirred for 1 hour and quenched with saturated $NH_4Cl$. The mixture was diluted with ethyl acetate and washed with $H_2O$ (2 times), and brine. The organic phase was dried over $MgSO_4$ and filtered and the filtrate was concentrated under reduced pressure. The residue was purified by silica gel chromatography, eluting with 3:1 hexanes:ethyl acetate to yield 17 (95 mg, 15% for two steps).

Step Three:

To a solution of 17 (116 mg, 0.54 mmol) in $CH_2Cl_2$ (3 ml) at room temperature under a dry nitrogen atmosphere, triethylamine (0.11 ml, 0.81 mmol) and methanesulfonyl chloride (0.053 ml, 0.68 mmol) were added dropwise by syringe. The resulting mixture was stirred for 15 minutes, was diluted with 1:1 hexanes:ethyl acetate and was washed with saturated $NaHCO_3$ and brine. The organic phase was dried over $MgSO_4$ and filtered and the filtrate was concentrated under reduced pressure to give 18 (153 mg) as a light yellow oil. This material was used without purification.

Step Four:

To a solution of 18 (150 mg, 0.51 mmol) in DMF (2 ml) cooled to 10° C. under a dry nitrogen atmosphere, sodium azide (66 mg, 1.0 mmol) was added. The resulting mixture was heated to 80° C. stirred for 2 hours, then was cooled to room temperature, diluted with 1:1 hexanes:ethyl acetate and washed with $H_2O$ (3 times) and brine. The organic phase was dried over $MgSO_4$ and filtered and the filtrate was concentrated under reduced pressure to give 19 (119 mg, 98%) as a light yellow oil. This material was used without purification.

Step Five:

To a solution of 19 (119 mg, 0.50 mmol) in THF (2 ml) at room temperature under a dry nitrogen atmosphere, $H_2O$ (0.092 ml, 5.1 mmol) and triphenylphosphine (401 mg, 1.53 mmol) were added. The resulting mixture was stirred for 44 hours at which time TLC indicated only partial conversion. Additional $H_2O$ (0.092 ml, 5.1 mmol) and triphenylphosphine (401 mg, 1.53 mmol) were added and the mixture was stirred for 4 days. The mixture was diluted with $CH_2Cl_2$ and was washed with approximately a 9:1 mixture of water/saturated $NaHCO_3$. The aqueous phase was extracted with $CH_2Cl_2$ (2 times) and the combined organic phases were dried over $MgSO_4$ and filtered. The filtrate was concentrated under reduced pressure and the resulting residue was purified by silica gel chromatography, eluting with 19:1 hexanes:ethyl acetate then 19:1 chloroform:methanol to yield 20 (75 mg, 70%) as a colorless oil.

Step Six:

To a solution of 20 (75 mg, 0.35 mmol) in 1,2-dichloroethane (2 ml) at room temperature under a dry nitrogen atmosphere, carbonyldiimidazole (62 mg, 0.38 mmol) was added. The resulting mixture was stirred for 2 hours and N,N-diisopropylethylamine (0.078 ml, 0.45 mmol) and 21 (101 mg, 0.41 mmol) were added. The mixture was heated to reflux for 14 hours, cooled to room temperature, then was diluted with ethyl acetate and was washed with HCl (2N) and brine. The organic phase was dried over $MgSO_4$ and filtered and the filtrate was concentrated under reduced pressure. The residue was purified by silica gel chromatography, eluting with 9:1 chloroform-:methanol then 4:1 chloroform:methanol to yield 22 (70 mg, 45%) as a pale yellow powder. $^1$H NMR (400 MHz, $CD_3SOCD_3$): δ 0.81 (t, J=6.6 Hz, 3H), 1.22 (m, 5H), 1.45 (m, 1H), 2.39 (m, 2H), 3.37 (m, overlaps $H_2O$, 1H), 3.63 (m, 1H), 4.60 (d, J=12.8 Hz, 1H), 4.64 (d, J=12.8 Hz, 1H), 4.91 (m, 1H), 5.93 (s overlapping m, 3H), 6.61 (m, 1H), 6.75 (m, 3H), 6.84 (br. s, 1H), 7.02 (m, 2H), 7.49 (d, J=5.12 Hz, 1H).

EXAMPLE 4

Synthesis of (9S,13S)-13-(1,3-benzodioxol-5-yl)-3,11-dioxo-1-phenyl-9-{[(2-thienylmethyl)amino]carbonyl}-2-oxa-4,10,12-triazapentadecan-15-oic acid (27).

Step One:

N-α-t-BOC-N-ε-CBZ-L-Lysine (400.0 mg, 1.05 mmol) and thiophene 2-methylamine (0.12 ml, 1.16 mmol) were dissolved in DMF (7 ml). To this was added 1-(3-dimethylaminopropyl)-3 ethylcarbodiimide hydrochloride (222 mg, 1.16 mmol), 1-hydroxybenzotriazole (157.0 mg, 1.16 mmol), and 4-methylmorpholine (0.16 ml, 1.16 mmol). The reaction was then stirred at room temperature for 24 hours. The mixture was taken up in ethyl acetate (200 ml), washed with water (2×100 ml), a saturated solution of sodium bicarbonate (100 ml), brine (100 ml), dried over $MgSO_4$, and concentrated under reduced pressure to give compound 23 (451.7 mg, 90%), which was used without further purification.

Step Two:

Compound 23 (451 mg, 0.95 mmol) was dissolved in 2 N HCl in dioxane (6 ml) and stirred at room temperature for 2 hours. The mixture was concentrated under reduced pressure and the residue was taken up in ethyl acetate (150 ml) and a saturated solution of sodium bicarbonate (150 ml). The organic layer was separated, dried over MgSO$_4$, and concentrated under reduced pressure to yield compound 24 (306.9 mg, 94%), which was used without further purification.

Step Three:

Compound 24 (128 mg, 0.37 mmol) and compound 25 (150 mg, 0.37 mmol) were dissolved in tetrahydrofuran (3 ml). Triethylamine (0.05 ml, 0.37 mmol) was added and the reaction stirred at room temperature for 24 hours. The mixture was diluted with ethyl acetate (100 ml) and washed several times with 0.5 N aqueous NaOH (5×25 ml), dried over MgSO$_4$, and concentrated under reduced pressure to yield compound 26 (235.3 mg, 99%), which was used without any further purification.

Step Four:

Compound 26 (230 mg, 0.36 mmol) was dissolved in methanol (3 ml), water (3 ml), and tetrahydrofuran (3 ml) and to this solution was added lithium hydroxide (45 mg, 1.08 mmol). The reaction was heated to 50° C. and stirred for 24 hours. The mixture was concentrated under reduced pressure and the residue was taken up in ethyl acetate (100 ml) and 0.5 N aqueous HCl (50 ml). The organic layer was separated, dried over MgSO$_4$, and concentrated under reduced pressure to yield 171.1 mg (78%) of compound 27. $^1$H NMR(400 MHz, DMSO-d$_6$): δ 8.5–8.6 (m, 1H), 7.3–7.4 (m, 6H), 7.1–7.2 (m, 1H), 6.9–7.0 (m, 2H), 6.85 (s, 1H), 6.7–6.8 (m, 2H), 6.5–6.6 (m, 2H), 5.9 (s, 2H), 5.0 (s, 2H), 4.8–4.9 (m, 1H), 4.3–4.5 (m, 2H), 4.0–4.1 (m, 1H), 2.9–3.0 (m, 2H), 2.4 (m, 2H), 1.5–1.6 (m, 2H), 1.3–1.5 (m, 2H), 1.1–1.3 (m, 2H).

EXAMPLE 5

Compound 34, (3S)-3-(1,3-benzodioxol-5-yl)-3-([((1S)-1-[(2-thienylmethyl)amino]carbonylpentyl)amino] carbonylamino)propanoic acid, of the structure shown below, was synthesized by the procedure of Example 4 by substituting t-BOC-L-norleucine for N-α-t-BOC-N-ε-CBZ-L-lysine in Step 1; mp 188–192° C.

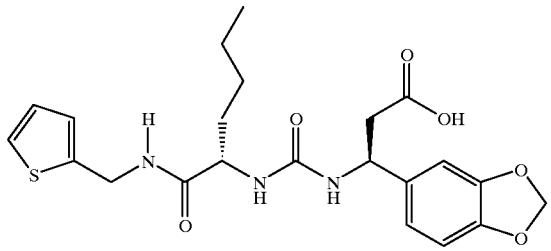

34

EXAMPLE 6

Compound 35, (3S)-3-(1,3-benzodioxol-5-yl)-3-([((1S)-1-[(2-acetylphenyl)amino]carbonylpentyl)amino] carbonylamino)propanoic acid, of the structure shown below, was synthesized by the procedure of Example 4 by starting with 2-aminoacetophenone and by substituting t-BOC-L-norleucine for N-α-t-BOC-N-ε-CBZ-L-lysine in Step 1.

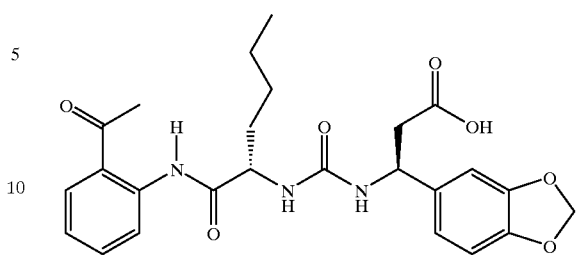

35

EXAMPLE 7

Compound 36, 3-(3S)-3-(1,3-benzodioxol-5-yl)-3-([((1S)-1-[(4-acetylphenyl)amino]carbonylpentyl)amino] carbonylamino)propanoic acid, of the structure shown below, was synthesized by the procedure of Example 4 by starting with 4-aminoacetophenone and by substituting t-BOC-L-norleucine for N-α-t-BOC-N-ε-CBZ-L-lysine in Step 1; mp 104–107° C.

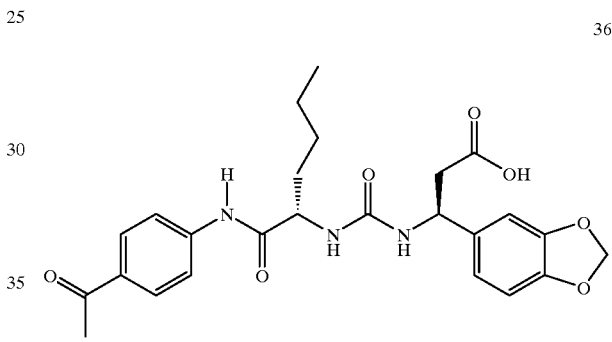

36

EXAMPLE 8

Compound 37, 3-(3S)-3-(1,3-benzodioxol-5-yl)-3-([((1S)-1-[(4-(2-thienylmethyl)aminobenzyl)amino] carbonylpentyl)amino]carbonylamino)propanoic acid, of the structure shown below, was synthesized by the procedure of Example 4 by starting with 4-(2-thienylmethylamino) benzylamine and by substituting t-BOC-L-norleucine for N-α-t-BOC-N-ε-CBZ-L-lysine in Step 1; mp 183–187° C.

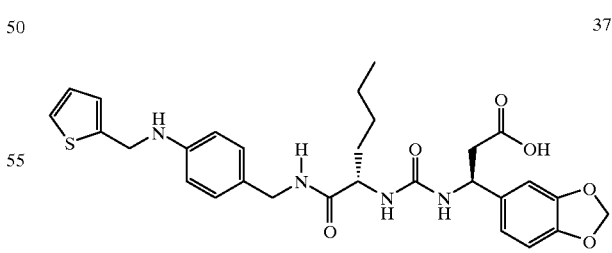

37

EXAMPLE 9

Compound 38, 3-(3S)-3-(1,3-benzodioxol-5-yl)-3-([((1S)-1-[(4-(2-methylbenzyloxy)-3-methoxybenzyl) amino]carbonylpentyl)amino]carbonylamino)propanoic acid, of the structure shown below, was synthesized by the procedure of Example 4 by starting with (4-(2- methylbenzyloxy)-3-methoxybenzylamine and by substituting t-BOC-L-norleucine for N-α-t-BOC-N-ε-CBZ-L-lysine in Step 1; mp 150–155° C.

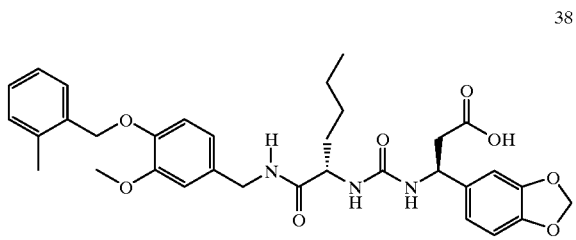

38

EXAMPLE 10

Compound 39, 3(3S)-3-(1,3-benzodioxol-5-yl)-3-([((1S)-1-[(4-(2-methylbenzyl)amino)benzyl)amnino]carbonylpentyl)amino]carbonylamino)propanoic acid, of the structure shown below, was synthesized by the procedure of Example 4 by starting with 4-(2-methylbenzylamino)benzylamine and by substituting t-BOC-L-norleucine for N-α-t-BOC-N-ε-CBZ-L-lysine in Step 1; mp 192–195° C.

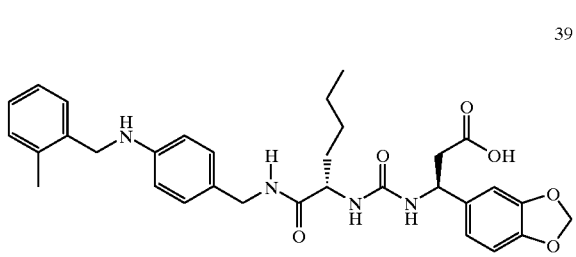

39

EXAMPLE 11

Compound 40, 3(3S)-3-(1,3-benzodioxol-5-yl)-3-([((1S)-1-[(4-(1,3-thiazol-2-ylmethyl)aminobenzyl)amino]carbonylpentyl)amino]carbonylamino)propanoic acid, of the strmcture shown below, was synthesized by the procedure of Example 4 starting with 4-[(1,3-thiazol-2-ylmethyl)amino]benzylamine and by substituting t-BOC-L-norleucine for N-α-t-BOC-N-ε-CBZ-L-lysine in Step 1; mp 190–195° C.

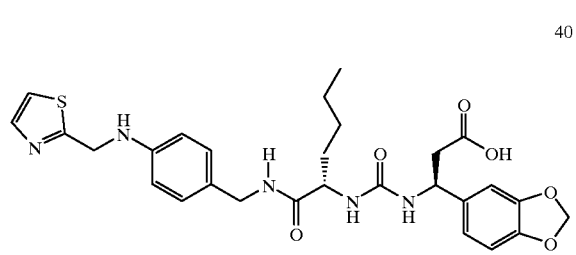

40

EXAMPLE 12

Compound 41, 3(3S)-3-(1,3-benzodioxol-5-yl)-3-([((1S)-1-[(4-(5-methyl-2-thienylmethyl)aminobenzyl)amino]carbonylpentyl)amino]carbonylamino)propanoic acid, of the structure shown below, was synthesized by the procedure of Example 4 by substituting 4-[(5-methyl)-2-thienylmethyl)amino]benzylamine and by substituting t-BOC-L-norleucine for N-α-t-BOC-N-ε-CBZ-L-lysine in Step 1; mp 195–198° C.

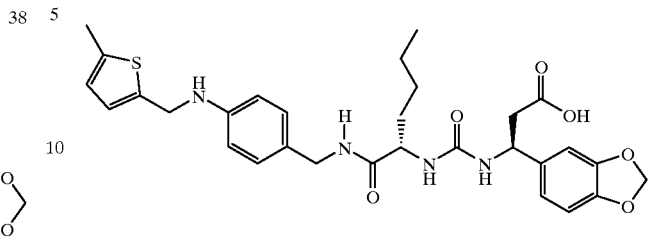

41

EXAMPLE 13

Compound 42, 3(3S)-3-(1,3-benzodioxol-5-yl)-3-([((1S)-1-[(4-(2-thienylsulfonamido)benzyl)amino]carbonylpentyl)amino]carbonylamino)propanoic acid of the structure shown below, may be synthesized by the procedure of Example 4 by starting with 4-(2-thienylsulfonamido)benzylamine and by substituting t-BOC-L-norleucine for N-α-t-BOC-N-ε-CBZ-L-lysine in Step 1.

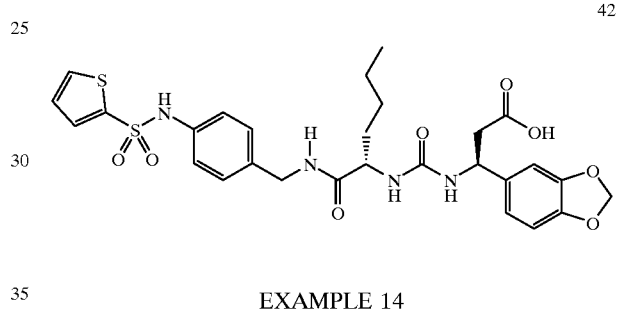

42

EXAMPLE 14

Compound 43, 3(3S)-3-(1,3-benzodioxol-5-yl)-3-([((1S)-1-[(4-(2-(6-methylpyridyl)methyl)benzyl)amino]carbonylpentyl)amino]carbonyl amino)propanoic acid, of the structure shown below, may be synthesized by the procedure of Example 4 by starting with 4-[2-(6-methyl)-pyridylmethyl)amino]benzylaminc and by substituting t-BOC-L-norleucine for N-α-t-BOC-N-ε-CBZ-L-lysine in Step 1; mp 186–191° C.

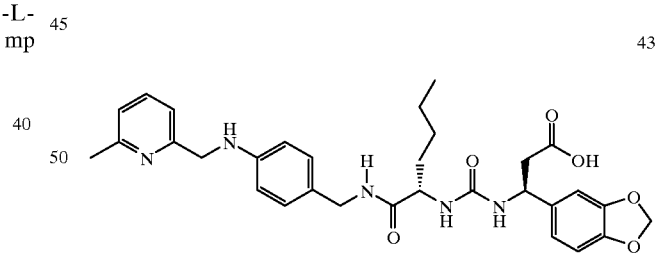

43

Synthetic procedures similar to those described above may be utilized to obtain the following compounds: 3-(1,3-benzodioxol-5-yl)-3-{[({(1R)-1-[(benzylsulfanyl)methyl]-2-methylpropyl}amino)carbonyl]amino}propanoic acid, 3-(1,3-benzodioxol-5-yl)-3-{[({(1S)-1-[(benzylsulfanyl)methyl]-2-methylpropyl}amino)carbonyl]amino}propanoic acid, 3-(1,3-benzodioxol-5-yl)-3-{[({(1S)-2-methyl-1-[(phenylsulfanyl)methyl]propyl}amino)carbonyl]amino}propanoic acid, 3-(1,3-benzodioxol-5-yl)-3-{[({(1S)-1-[(benzylsulfonyl)methyl]-2-methylpropyl}amino)carbonyl]amino}propanoic acid, 3-(1,3-benzodioxol-5-yl)-3-({[((1S)-1-{[(4-methoxybenzyl)amino]carbonyl}-3- methylbutyl)amino]carbonyl}amino)propanoic acid, 3-(1,3-benzodioxol-5-yl)-3-({[((1R)-1-{[(4-methoxybenzyl)amino]carbonyl}-3-methylbutyl)amino]carbonyl}amino) propanoic acid, (3R)-3-(1,3-benzodioxol-5-yl)-3-{[({(1S)-2-methyl-1-[(phenylsulfanyl)methyl]propyl}amino) carbonyl]amino}propanoic acid, (3S)-3-(1,3-benzodioxol-5-yl)-3-(((((1S)-2-methyl-1-((phenylsulfanyl)methyl) propyl)amino)carbonyl)amino)propanoic acid, (3S)-3-[({[1-{[bis-(phenylsulfanyl)]methyl}-2-methylpropyl]amino}carbonyl)amino]-3-[(3,4-methylenedioxy)phenyl] propanoic acid, (3S)-3-(1,3-benzodioxol-5-yl)-3-[[({(1S)-2-methyl-1-[(phenethylsulfanyl)methyl]propyl}amino) carbonyl]amino}propanoic acid, (3S)-3-(1,3-benzodioxol-5-yl)-3-(([(((1S)-2-methyl-1-{[(3-phenylpropyl)sulfanyl] methyl}propyl)amino]carbonyl}amino)propanoic acid, (9S,13S)-13-(1,3-benzodioxol-5-yl)-3,11-dioxo-1-phenyl-9-[({4-[(2-toluidinocarbonyl)amino]benzyl}amino)carbonyl]-2-oxa-4,10,12-triazapentadecan-15-oic acid, (9S,13S)-13-(1,3-benzodioxol-5-yl)-9-{[(4-hydroxyphenethyl)amino] carbonyl}-3,11-dioxo-1-phenyl-2-oxa-4,10,12-triazapentadecan-15-oic acid, (9S,13S)-13-(1,3-benzodioxol-5-yl)-3,11-dioxo-1-phenyl-9-({[2-(2-pyridinyl)ethyl]amino}carbonyl)-2-oxa-4,10,12-triazapentadecan-15-oic acid, 3-(1,3-benzodioxol-5-yl)-3-{[({(1S)-3-methyl-1-[({4-[(2-toluidinocarbonyl)amino] benzyl}amino)carbonyl]butyl}amino)carbonyl] amino}propanoic acid, (3S)-3-(1,3-benzodioxol-5-yl)-3-((((((1S)-3-(methylsulfanyl)-1-((phenylsulfanyl)methyl) propyl)amino)carbonyl)amino)propanoic acid, (3S)-3-(1,3-benzodioxol-5-yl)-3-{[({(1S)-3-methyl-1-[(phenylsulfanyl) methyl]butyl}amino)carbonyl]amino}propanoic acid, (8S,12S)-12-(1,3-benzodioxol-5-yl)-3,10-dioxo-8-((phenylsulfanyl)methyl)-2-oxa-4,9,11-triazatetradecan-14-oic acid, (9S,13S)-13-(1,3-benzodioxol-5-yl)-3,11-dioxo-9-[(phenylsulfanyl)methyl]-2-oxa-4,10,12-triazapentadecan-15-oic acid, (9S,13S)-13-(1,3-benzodioxol-5-yl)-3,11-dioxo-9-({[3-(2-oxo-1-pyrrolidinyl)propyl] amino}carbonyl)-1-phenyl-2-oxa-4,10,12-triazapentadecan-15-oic acid, (9S,13S)-13-(1,3-benzodioxol-5-yl)-9-({[2-(1H-indol-3-yl)ethyl] amino}carbonyl)-3,11-dioxo-2-oxa-4,10,12-triazapentadecan-15-oic acid, (9S,13S)-9-{[(1H-benzimidazol-2-ylmethyl)amino]carbonyl}-13-(1,3-benzodioxol-5-yl)-3,11-dioxo-2-oxa-4,10,12-triazapentadecan-15-oic acid, (9S,13S)-13-(1,3-benzodioxol-5-yl)-3,11-dioxo-9-{[(4-piperidinylmethyl) amino]carbonyl}-2-oxa-4,10,12-triazapentadecan-15-oic acid, (9S,13S)-13-(1,3-benzodioxol-5-yl)-3,11-dioxo-1-phenyl-9-{[(2-thienylmethyl)amino]carbonyl}-2-oxa-4,10,12-triazapentadecan-15-oic acid, (9S,13S)-13-(1,3-benzodioxol-5-yl)-9-{[(3-hydroxy-4-methoxybenzyl) amino]carbonyl}-3,11-dioxo-2-oxa-4,10,12-triazapentadecan-15-oic acid, (9S,13S)-13-(1,3-benzodioxol-5-yl)-9-{[(4-hydroxyphenethyl)amino] carbonyl}-3,11-dioxo-2-oxa-4,10,12-triazapentadecan-15-oic acid, (9S,13S)-9-{[(4-aminobenzyl)amino]carbonyl}-13-(1,3-benzodioxol-5-yl)-3,11-dioxo-2-oxa-4,10,12-triazapentadecan-15-oic acid, (9S,13S)-13-(1,3-benzodioxol-5-yl)-3,11-dioxo-9-[(phenylsulfonyl)methyl]-2-oxa-4,10,12-triazapentadecan-15-oic acid, (9S,13S)-13-(1,3-benzodioxol-5-yl)-9-[({4-[bis(2-methylbenzyl)amino] benzyl}amino)carbonyl]-3,11-dioxo-2-oxa-4,10,12-triazapentadecan-15-oic acid, (3S)-3-[({[(1S)-1-({[4-(acetylamino)phenyl]sulfanyl}methyl)-3-(methylsulfanyl) propyl]amino}carbonyl)amino]-3-(1,3-benzodioxol-5-yl) propanoic acid, (3S)-3-(1,3-benzodioxol-5-yl)-3-[({[(1S)-1-{[(4-methoxyphenyl)sulfanyl]methyl}-3-(methylsulfanyl) propyl]amino}carbonyl)amino]propanoic acid, (3S)-3-[({[(1S)-1-{[(4-aminophenyl)sulfanyl]methyl}-3-(methylsulfanyl)propyl]amino}carbonyl)amino]-3-(1,3-benzodioxol-5-yl)propanoic acid, (3S)-3-(1,3-benzodioxol-5-yl)-3-[({[(1S)-1-{[(4-chlorophenyl)sulfanyl]methyl}-3-(methylsulfanyl)propyl]amino}carbonyl)amino]propanoic acid, (3S)-3-(1,3-benzodioxol-5-yl)-3-{[({(1S)-2-(benzylsulfanyl)-1-[(phenylsulfanyl)methyl]ethyl}amino) carbonyl]amino}propanoic acid, (3S)-3-(1,3-benzodioxol-5-yl)-3-[({[(1S)-1-[({4-[(benzylsulfonyl)amino] phenyl}sulfanyl)methyl]-3-(methylsulfanyl)propyl] amino}carbonyl)amino]propanoic acid, (3S)-3-(1,3-benzodioxol-5-yl)-3-{[({(1S)-3-(methylsulfanyl)-1-[({4-[(methylsulfonyl)amino]phenyl}sulfanyl)methyl] propyl}amino)carbonyl]amino}propanoic acid, (3S)-3-(1,3-benzodioxol-5-yl)-3-[({[(1S)-1-{[(4-{[(4-methylphenyl)sulfonyl]amino}phenyl)sulfanyl]methyl}-3-(methylsulfanyl)propyl]amino}carbonyl)amino]propanoic acid, 3-{[({(1S)-3-(methylsulfanyl)-1-[(phenylsulfanyl) methyl]propyl}amino)carbonyl]amino}propanoic acid, (3S)-3-(1,3-benzodioxol-5-yl)-3-{[({(1S)-3-(methylsulfanyl)-1-[({4-[(2-toluidinocarbonyl)amino] phenyl}sulfanyl)methyl]propyl}amino)carbonyl] amino}propanoic acid, (2S)-2-({[((1S)-5-{[(benzyloxy) carbonyl]amino}-1-{[(2-thienylmethyl)amino] carbonyl}pentyl)amino]carbonyl}amino)butanedioic acid, (3S)-3-(1,3-benzodioxol-5-yl)-3-{[({(1S)-2-(ethylsulfanyl)-1-[(phenylsulfanyl)methyl]ethyl}amino)carbonyl] amino}propanoic acid, (3S)-3-(1,3-benzodioxol-5-yl)-3-{[({(1S)-2-(methylsulfanyl)-1-[(phenylsulfanyl)methyl] ethyl}amino)carbonyl]amino}propanoic acid, N,N'-bis[(1S)-1-(1,3-benzodioxol-5-yl)-2-carboxyethyl]urea, (9S,13S)-13-(1,3-benzodioxol-5-yl)-9-[({4-[(2-methylbenzyl) amino]benzyl}amino)carbonyl]-3,11-dioxo-1-phenyl-2-oxa-4,10,12-triazapentadecan-15-oic acid, (3S)-3-(1,3-benzodioxol-5-yl)-3-((((1R)-2-(benzylsulfonyl)-1-((phenylsulfanyl)methyl)ethyl)amino)carbonyl)amino) propanoic acid, (3S)-3-(1,3-benzodioxol-5-yl)-3-{[({(1S)-1-[(phenylsulfanyl)methyl]pentyl}amino)carbonyl] amino}propanoic acid, (3S)-3-(1,3-benzodioxol-5-yl)-3-[({[(1S)-1-(1,3-benzodioxol-5-yl)-3-(tert-butoxy)-3-oxopropyl]amino}carbonyl)amino]propanoic acid, (3S)-3-[({[(1S)-1-{[(2-aminophenyl)sulfanyl]methyl}-3-(methylsulfanyl)propyl]amino}carbonyl)amino]-3-(1,3-benzodioxol-5-yl)propanoic acid, (3S)-3-(1,3-benzodioxol-5-yl)-3-[({[(1S)-1-{[(2-methylphenyl)sulfanyl]methyl}-3-(methylsulfanyl)propyl]amino}carbonyl)amino]propanoic acid, (3S)-3-(1,3-benzodioxol-5-yl)-3-[({[(1S)-1-{[(3-methylphenyl)sulfanyl]methyl}-3-(methylsulfanyl)propyl] amino}carbonyl)amino]propanoic acid, (3S)-3-(1,3-benzodioxol-5-yl)-3-(((2-(phenylsulfanyl)ethylamino) carbonyl)amino)propanoic acid, (3S)-3-(1,3-benzodioxol-5-yl)-3-{[({(1S)-2-[(3-phenylpropyl)sulfanyl]-1-[(phenylsulfanyl)methyl]ethyl}amino)carbonyl] amino}propanoic acid, (3S)-3-(1,3-benzodioxol-5-yl)-3-{[({(1S)-2-(phenylsulfanyl)-1-[(propylsulfanyl)methyl] ethyl}amino)carbonyl]amino}propanoic acid, (3S)-3-(1,3-benzodioxol-5-yl)-3-{[({(1S)-3-(methylsulfanyl)-1-[(phenylsulfanyl)methyl]propyl}amino)carbothioyl] amino}propanoic acid, (3S)-4-(methylsulfanyl)-3-{[({(1S)-3-(methylsulfanyl)-1-[(phenylsulfanyl)methyl] propyl}amino)carbonyl]amino}butanoic acid, (3S)-3-{[({(1S)-3-(methylsulfanyl)-1-[(phenylsulfanyl)methyl] propyl}amino)carbonyl]amino}-4-(phenylsulfanyl)butanoic acid, (3S)-3-(1,3-benzodioxol-5-yl)-3-[({[(1S)-1-methyl-2-(phenylsulfanyl)ethyl]amino}carbonyl)amino]propanoic acid, (3S)-3-(1,3-benzodioxol-5-yl)-3-{[({(1S)-2-

(octylsulfanyl)-1-[(phenylsulfanyl)methyl]ethyl}amino) carbonyl]amino}propanoic acid, (3S)-3-(1,3-benzodioxol-5-yl)-3-{[({(1S)-3-(methylsulfanyl)-1-[({3-[(2-toluidinocarbonyl)amino]phenyl}sulfanyl)methyl] propyl}amino)carbonyl]amino}propanoic acid, (3S)-3-(1,3-benzodioxol-5-yl)-3-[({[(1S)-3-(methylsulfanyl)-1-(phenoxymethyl)propyl]amino}carbonyl)amino]propanoic acid, (3S)-3-(1,3-benzodioxol-5-yl)-3-{[(methyl {(1S)-3-(methylsulfanyl)-1-[(phenylsulfanyl)methyl]propyl}amino) carbonyl]amino}propanoic acid, (3S)-3-(1,3-benzodioxol-5-yl)-3-{[({1-[(phenylsulfanyl)methyl]pentyl}oxy) carbonyl]amino}propanoic acid, (3S)-3-(1,3-benzodioxol-5-yl)-3-{[({2-(phenylsulfanyl)-1-[(phenylsulfanyl)methyl] ethyl}amino)carbonyl]amino}propanoic acid, (3S)-3-(1,3-benzodioxol-5-yl)-3-{[({(1S)-2-[(carboxymethyl)sulfanyl]-1-[(phenylsulfanyl)methyl]ethyl}amino)carbonyl] amino}propanoic acid, (3S)-3-[({[(1S)-1-{[(3-aminophenyl)thio]methyl}-3-(methylthio)propyl] amino}carbonyl)amino]-3-(1,3-benzodioxol-5-yl)propanoic acid, (3S)-3-(1,3-benzodioxol-5-yl)-3-[({[(1S)-1-[({4-[(2-methylbenzyl)amino]phenyl}thio)methyl]-3-(methylthio) propyl]amino}carbonyl)amino]propanoic acid, (3S)-3-(1,3-benzodioxol-5-yl)-3-[({[(1S)-1-[({3-[(methylsulfonyl) amino]phenyl}thio)methyl]-3-(methylthio)propyl] amino}carbonyl)amino]propanoic acid, (3S)-3-(1,3-benzodioxol-5-yl)-3-{[({(1S)-3-(methylthio)-1-[({3-[(propylsulfonyl)amino]phenyl}thio)methyl]propyl}amino) carbonyl]amino}propanoic acid, (3S)-3-{[({(1S)-2-(allyloxy)-1-[(phenylthio)methyl]ethyl}amino)carbonyl] amino}-3-(1,3-benzodioxol-5-yl)propanoic acid, (3S)-3-(1,3-benzodioxol-5-yl)-3-{[({(1S)-2-(benzyloxy)-1-[(phenylthio)methyl]ethyl}amino)carbonyl] amino}propanoic acid, (3S)-3-(1,3-benzodioxol-5-yl)-3-[({[(1R)-1-phenyl-2-(propylthio)ethyl]amino}carbonyl) amino]propanoic acid, (3S)-3-(1,3-benzodioxol-5-yl)-3-(((((1R)-1-benzyl-2-(propylthio)ethyl)amino)carbonyl) amino)propanoic acid, (3S)-3-(1,3-benzodioxol-5-yl)-3-{[({(1S)-3-(phenylthio)-1-[(phenylthio)methyl]propyl}amino) carbonyl]amino}propanoic acid, (3S)-3-(1,3-benzodioxol-5-yl)-3-{[({(1S)-4-hydroxy-1-[(phenylthio)methyl] butyl}amino)carbonyl]amino}propanoic acid, (3S)-3-(1,3-benzodioxol-5-yl)-3-{[({(1S)-2-ethoxy-1-[(phenylthio) methyl]ethyl}oxy)carbonyl]amino}propanoic acid, (3S)-3-(1,3-benzodioxol-5-yl)-3-{[({(1S)-2-(phenethyloxy)-1-[(phenylthio)methyl]ethyl}oxy)carbonyl]amino}propanoic acid, (3S)-3-(1,3-benzodioxol-5-yl)-3-{[({(1S)-2-[(cyclopropylmethyl)thio]-1-[(phenylthio)methyl] ethyl}amino)carbonyl]amino}propanoic acid, (3S)-3-(1,3-benzodioxol-5-yl)-3-{[({(1R)-2-(benzyloxy)-1-[(benzylthio)methyl]ethyl}amino)carbonyl] amino}propanoic acid, (3S)-3-(1,3-benzodioxol-5-yl)-3-{[({(1R)-2-(benzyloxy)-1-[(benzylthio)methyl]ethyl}oxy) carbonyl]amino}propanoic acid, (3S)-3-(1,3-benzodioxol-5-yl)-3-{[({(1R)-2-(benzyloxy)-1-[(ethylthio)methyl] ethyl}oxy)carbonyl]amino}propanoic acid, (3S)-3-(1,3-benzodioxol-5-yl)-3-{[({(1S)-2-(ethylthio)-1-[(phenylthio) methyl]ethyl}oxy)carbonyl]amino}propanoic acid, (3S)-3-(1,3-benzodioxol-5-yl)-3-{[({(1S)-2-(benzylthio)-1-[(phenylthio)methyl]ethyl}oxy)carbonyl]amino}propanoic acid, (3S)-3-(1,3-benzodioxol-5-yl)-3-{[({(1S)-1-[({4-[(2-toluidinocarbonyl)amino]phenyl}thio)methyl]pentyl}oxy) carbonyl]amino}propanoic acid, (3S)-3-(1,3-benzodioxol-5-yl)-3-{[({(1S)-1-[({3-[(2-methylbenzyl)amino] phenyl}thio)methyl]pentyl}oxy)carbonyl]amino}propanoic acid, (3S)-3-(1,3-benzodioxol-5-yl)-3-{[({(1S)-2-{[(4-methylphenyl)sulfonyl]amino}-1-[(phenylthio)methyl] ethyl}amino)carbonyl]amino}propanoic acid, (3S)-3-(1,3-benzodioxol-5-yl)-3-{[({(1S)-1-[(2-thienylmethoxy) methyl]pentyl}amino)carbonyl]amino}propanoic acid, and pharmaceutically acceptable salts thereof.

EXAMPLE 15

The ability of compounds of the present invention to inhibit binding is described in detail hereinafter in the Examples by a procedure in which a 26-amino acid peptide containing the CS1 sequence of fibronectin with an N-terminal Cys was coupled to maleimide activated ovalbumin. Ovalbumin and CS1 conjugated ovalbumin were coated onto 96-well polystyrene plates at 5 μg/ml in TBS (50 mM Tris, pH 7.5; 150 mM NaCl) at 4° C. for 16 hours. The plates were washed three times with TBS and blocked with TBS containing 3% BSA at room temperature for 4 hours. Blocked plates were washed three times in binding buffer (TBS; 1 mM $MgCl_2$; 1 mM $CaCl_2$; 1 mM $MnCl_2$) prior to assay. Ramos cells fluorescently labeled with calcein AMC-3099 were resuspended in binding buffer ($10^7$ cells/ml) and diluted 1:2 with same buffer with or without compound. The cells were added immediately to the wells ($2.5 \times 10^5$ cells/ well) and incubated for 30 minutes at 37° C. Following three washes with binding buffer, adherent cells were lysed and quantitated using a fluorometer.

The results are shown in Tables 1 and 2. $IC_{50}$ is defined as the dose required to give 50% inhibition. The lower the $IC_{50}$ value and the greater the percentage of inhibition, the more efficient the compound is at prevention of cell adhesion. A stands for inhibition in Table 1, and the percent inhibition indicates the inhibition of cell adhesion when compound is included in the assay at a concentration of 100 μM.

TABLE 1

| Compound | $IC_{50}$ | % A |
|---|---|---|
| 3-(1,3-benzodioxol-5-yl)-3-{[({(1R)-1-[(benzylsulfanyl)methyl]-2-methylpropyl} amino)carbonyl]amino}propanoic acid | 40 | 83 |
| 3-(1,3-benzodioxol-5-yl)-3-{[({(1S)-1-[(benzylsulfanyl)methyl]-2-methylpropyl} amino)carbonyl]amino}propanoic acid | 10 | 100 |
| 3-(1,3-benzodioxol-5-yl)-3-{[({(1S)-2-methyl-1-[(phenylsulfanyl)methyl]propyl} amino)carbonyl]amino}propanoic acid | 5 | 99 |
| 3-(1,3-benzodioxol-5-yl)-3-{[({(1S)-1-[(benzylsulfonyl)methyl]-2-methylpropyl} amino)carbonyl]amino}propanoic acid | 35 | 92 |
| 3-(1,3-benzodioxol-5-yl)-3-({[((1S)-1-{[(4-methoxybenzyl)amino]carbonyl}-3-methyl butyl)amino]carbonyl}amino)propanoic acid | 0.5 | 100 |
| 3-(1,3-benzodioxol-5-yl)-3-({[((1R)-1-{[(4-methoxybenzyl)amino]carbonyl}-3-methyl butyl)amino]carbonyl}amino)propanoic acid | 45 | 66 |

TABLE 1-continued

| Compound | IC$_{50}$ | % A |
|---|---|---|
| (3R)-3-(1,3-benzodioxol-5-yl)-3-{[({(1S)-2-methyl-1-[(phenylsulfanyl)methyl]propyl}amino)carbonyl]amino}propanoic acid | 35 | 83 |
| (3S)-3-(1,3-benzodioxol-5-yl)-3-(((((1S)-2-methyl-1-((phenylsulfanyl)methyl)propyl)amino)carbonyl)amino)propanoic acid | 2.5 | 100 |
| (3S)-3-[({[1-{[bis-(phenylsulfanyl)]methyl}-2-methylpropyl]amino}carbonyl)amino]-3-[(3,4-methylenedioxy)phenyl]propanoic acid | 35 | 95 |
| (3S)-3-(1,3-benzodioxol-5-yl)-3-{[({(1S)-2-methyl-1-[(phenethylsulfanyl)methyl]propyl}amino)carbonyl]amino}propanoic acid | 20 | 98 |
| (3S)-3-(1,3-benzodioxol-5-yl)-3-({[((1S)-2-methyl-1-{[(3-phenylpropyl)sulfanyl]methyl}propyl)amino]carbonyl}amino)propanoic acid | 20 | 99 |
| (9S,13S)-13-(1,3-benzodioxol-5-yl)-3,11-dioxo-1-phenyl-9-[({4-[(2-toluidino carbonyl)amino]benzyl}amino)carbonyl]-2-oxa-4,10,12-triazapentadecan-15-oic acid | 0.0003 | 100 |
| (9S,13S)-13-(1,3-benzodioxol-5-yl)-9-{[(4-hydroxyphenethyl)amino]carbonyl}-3,11-dioxo-1-phenyl-2-oxa-4,10,12-triazapentadecan-15-oic acid | 2 | 100 |
| (9S,13S)-13-(1,3-benzodioxol-5-yl)-3,11-dioxo-1-phenyl-9-({[2-(2-pyridinyl)ethyl]amino}carbonyl)-2-oxa-4,10,12-triazapentadecan-15-oic acid | 2 | 100 |
| 3-(1,3-benzodioxol-5-yl)-3-{[({(1S)-3-methyl-1-[({4-[(2-toluidinocarbonyl)amino]benzyl}amino)carbonyl]butyl}amino)carbonyl]amino}propanoic acid | 0.02 | 100 |
| (9S,13S)-13-(1,3-benzodioxol-5-yl)-9-({[2-(1H-indol-3-yl)ethyl]amino}carbonyl)-3,11-dioxo-2-oxa-4,10,12-triazapentadecan-15-oic acid | 45 | 78 |
| (3S)-3-(1,3-benzodioxol-5-yl)-3-{[({(1S)-3-methyl-1[(phenylsulfanyl)methyl]butyl}amino)carbonyl]amino}propanoic acid | 2 | 100 |
| (3S)-3-(1,3-benzodioxol-5-yl)-3-(((((1S)-3-(methylsulfanyl)-1-((phenylsulfanyl)methyl)propyl)amino)carbonyl)amino)propanoic acid | 0.3 | 100 |
| (9S,13S)-13-(1,3-benzodioxol-5-yl)-3,11-dioxo-9-[(phenylsulfanyl)methyl]-2-oxa-4,10,12-triazapentadecan-15-oic acid | 0.4 | 100 |
| (8S,12S)-12-(1,3-benzodioxol-5-yl)-3,10-dioxo-8-((phenylsulfanyl)methyl)-2-oxa-4,9,11-triazatetradecan-14-oic acid | 2 | 100 |
| (9S,13S)-13-(1,3-benzodioxol-5-yl)-3,11-dioxo-9-({[3-(2-oxo-1-pyrrolidinyl)propyl]amino}carbonyl)-1-phenyl-2-oxa-4,10,12-triazapentadecan-15-oic acid | 3 | 100 |
| (9S,13S)-13-(1,3-benzodioxol-5-yl)-9-({[2-(1H-indol-3-yl)ethyl]amino}carbonyl)-3,11-dioxo-2-oxa-4,10,12-triazapentadecan-15-oic acid | 3.5 | 100 |
| (9S,13S)-9-{[(1H-benzimidazol-2-ylmethyl)amino]carbonyl}-13-(1,3-benzodioxol-5-yl)-3,11-dioxo-2-oxa-4,10,12-triazapentadecan-15-oic acid | 2 | 100 |
| (9S,13S)-13-(1,3-benzodioxol-5-yl)-3,11-dioxo-9-{[(4-piperidinylmethyl)amino]carbonyl}-2-oxa-4,10,12-triazapentadecan-15-oic acid | 5 | 97 |
| (9S,13S)-13-(1,3-benzodioxol-5-yl)-3,11-dioxo-1-phenyl-9-{[(2-thienylmethyl)amino]carbonyl}-2-oxa-4,10,12-triazapentadecan-15-oic acid, 27 | 0.2 | 100 |
| (9S,13S)-13-(1,3-benzodioxol-5-yl)-9-{[(3-hydroxy-4-methoxybenzyl)amino]carbonyl}-3,11-dioxo-2-oxa-4,10,12-triazapentadecan-15-oic acid | 0.2 | 100 |
| (9S,13S)-13-(1,3-benzodioxol-5-yl)-9-{[(4-hydroxyphenethyl)amino]carbonyl}-3,11-dioxo-2-oxa-4,10,12-triazapentadecan-15-oic acid | 6 | 100 |
| (9S,13S)-9-{[(4-aminobenzyl)amino]carbonyl}-13-(1,3-benzodioxol-5-yl)-3,11-dioxo-2-oxa-4,10,12-triazapentadecan-15-oic acid | 0.3 | 100 |
| (9S,13S)-13-(1,3-benzodioxol-5-yl)-3,11-dioxo-9-[(phenylsulfonyl)methyl]-2-oxa-4,10,12-triazapentadecan-15-oic acid | >100 | 20 |
| (9S,13S)-13-(1,3-benzodioxol-5-yl)-9-[({4-bis(2-methylbenzyl)amino]benzyl}amino)carbonyl]-3,11-dioxo-2-oxa-4,10,12-triazapentadecan-15-oic acid | 1 | 95 |
| (3S)-3-[({[(1S)-1-({[4-(acetylamino)phenyl]sulfanyl}methyl)-3-(methylsulfanyl)propyl]amino}carbonyl)amino]-3-(1,3-benzodioxol-5-yl)propanoic acid | 3 | 100 |
| (3S)-3-(1,3-benzodioxol-5-yl)-3-[({[(1S)-1-{[(4-methoxyphenyl)sulfanyl]methyl}-3-(methylsulfanyl)propyl]amino}carbonyl)amino]propanoic acid | 7 | 100 |
| (3S)-3-[({[(1S)-1-{[(4-aminophenyl)sulfanyl]methyl}-3-(methylsulfanyl)propyl]amino}carbonyl)amino]-3-(1,3-benzodioxol-5-yl)propanoic acid | 3 | 100 |
| (3S)-3-(1,3-benzodioxol-5-yl)-3-[({[(1S)-1-{[(4-chlorophenyl)sulfanyl]methyl}-3-(methylsulfanyl)propyl]amino}carbonyl)amino]propanoic acid | 3 | 100 |
| (3S)-3-(1,3-benzodioxol-5-yl)-3-{[({(1S)-2-(benzylsulfanyl)-1-[(phenylsulfanyl)methyl]ethyl}amino)carbonyl]amino}propanoic acid | 0.02 | 100 |
| (3S)-3-(1,3-benzodioxol-5-yl)-3-[({[(1S)-1-[({4-[(benzylsulfonyl)amino]phenyl}sulfanyl)methyl]-3-(methylsulfanyl)propyl]amino}carbonyl)amino]propanoic acid | 0.3 | 100 |
| (3S)-3-(1,3-benzodioxol-5-yl)-3-{[({(1S)-3-(methylsulfanyl)-1-[({4-[(methylsulfonyl)amino]phenyl}sulfanyl)methyl]propyl}amino)carbonyl]amino}propanoic acid | 0.5 | 100 |
| (3S)-3-(1,3-benzodioxol-5-yl)-3-[({[(1S)-1-{[(4-{[(4-methylphenyl)sulfonyl]amino}phenyl)sulfanyl]methyl}-3-(methylsulfanyl)propyl]amino}carbonyl)amino]propanoic acid | 0.4 | 100 |
| 3-{[({(1S)-3-(methylsulfanyl)-1-[(phenylsulfanyl)methyl]propyl}amino)carbonyl]amino}propanoic acid | 25 | 96 |
| (3S)-3-(1,3-benzodioxol-5-yl)-3-{[({(1S)-3-(methylsulfanyl)-1-[({4-[(2-toluidino carbonyl)amino]phenyl}sulfanyl)methyl]propyl}amino)carbonyl]amino}propanoic acid | 0.0009 | 100 |
| (2S)-2-({[((1S)-5-{[(benzyloxy)carbonyl]amino}-1-{[(2-thienylmethyl)amino]carbonyl}pentyl]amino}carbonyl)amino)butanedioic acid | 45 | 89 |
| (3S)-3-(1,3-benzodioxol-5-yl)-3-{[({(1S)-2-(ethylsulfanyl)-1-[(phenylsulfanyl)methyl]ethyl}amino)carbonyl]amino}propanoic acid | 0.05 | 100 |
| (3S)-3-(1,3-benzodioxol-5-yl)-3-{[({(1S)-2-(methylsulfanyl)-1-[(phenylsulfanyl)methyl]ethyl}amino)carbonyl]amino}propanoic acid | 0.1 | 100 |

TABLE 1-continued

| Compound | IC$_{50}$ | % A |
|---|---|---|
| N,N'-bis[(1S)-1-(1,3-benzodioxol-5-yl)-2-carboxyethyl]urea | 7 | 99 |
| (9S,13S)-13-(1,3-benzodioxol-5-yl)-9-[({4-[(2-methylbenzyl)amino]benzyl}amino) carbonyl]-3,11-dioxo-1-phenyl-2-oxa-4,10,12-triazapentadecan-15-oic acid | 0.0004 | 100 |
| (3S)-3-(1,3-benzodioxol-5-yl)-3-(((((1R)-2-(benzylsulfonyl)-1-((phenylsulfanyl)methyl)ethyl)amino)carbonyl)amino)propanoic acid | 1 | 100 |
| (3S)-3-(1,3-benzodioxol-5-yl)-3-{[({(1S)-1-[(phenylsulfanyl)methyl]pentyl}amino) carbonyl]amino}propanoic acid | 0.4 | 100 |
| (3S)-3-(1,3-benzodioxol-5-yl)-3-[({[(1S)-1-(1,3-benzodioxol-5-yl)-3-(tert-butoxy)-3-oxopropyl]amino}carbonyl)amino]propanoic acid | 4 | 100 |
| (3S)-3-[({[(1S)-1-{[(2-aminophenyl)sulfanyl]methyl}-3-(methylsulfanyl)propyl] amino}carbonyl)amino]-3-(1,3-benzodioxol-5-yl)propanoic acid | 0.3 | 100 |
| (3S)-3-(1,3-benzodioxol-5-yl)-3-[({[(1S)-1-{[(2-methylphenyl)sulfanyl]methyl}-3-(methylsulfanyl)propyl]amino}carbonyl)amino]propanoic acid | 0.3 | 100 |
| (3S)-3-(1,3-benzodioxol-5-yl)-3-[({[(1S)-1-{[(3-methylphenyl)sulfanyl]methyl}-3-(methylsulfanyl)propyl]amino}carbonyl)amino]propanoic acid | 0.3 | 100 |
| (3S)-3-(1,3-benzodioxol-5-yl)-3-[({[2-(phenylsulfanyl)ethyl]amino}carbonyl)amino] propanoic acid | 6 | 100 |
| (3S)-3-(1,3-benzodioxol-5-yl)-3-{[({(1S)-2-[(3-phenylpropyl)sulfanyl]-1-[(phenyl sulfanyl)methyl]ethyl}amino)carbonyl]amino}propanoic acid | 2 | 100 |
| (3S)-3-(1,3-benzodioxol-5-yl)-3-{[({(1S)-2-(phenylsulfanyl)-1-[(propylsulfanyl) methyl]ethyl}amino)carbonyl]amino}propanoic acid | 0.5 | 100 |
| (3S)-3-(1,3-benzodioxol-5-yl)-3-{[({(1S)-3-(methylsulfanyl)-1-[(phenylsulfanyl) methyl]propyl}amino)carbothioyl]amino}propanoic acid | 3 | 100 |
| (3S)-4-(methylsulfanyl)-3-{[({(1S)-3-(methylsulfanyl)-1-[(phenylsulfanyl)methyl] propyl}amino)carbonyl]amino}butanoic acid | 8 | 99 |
| (3S)-3-{[({(1S)-3-(methylsulfanyl)-1-[(phenylsulfanyl)methyl]propyl}amino) carbonyl]amino}-4-(phenylsulfanyl)butanoic acid, 8 | 4 | 100 |
| (3S)-3-(1,3-benzodioxol-5-yl)-3-[({[(1S)-1-methyl-2-(phenylsulfanyl)ethyl]amino} carbonyl)amino]propanoic acid | 3 | 100 |
| (3S)-3-(1,3-benzodioxol-5-yl)-3-{[({(1S)-2-(octylsulfanyl)-1-[(phenylsulfanyl)methyl] ethyl}amino)carbonyl]amino}propanoic acid | 5 | 98 |
| (3S)-3-(1,3-benzodioxol-5-yl)-3-{[({(1S)-3-(methylsulfanyl)-1-[({3-[(2-toluidino carbonyl)amino]phenyl}sulfanyl)methyl]propyl}amino)carbonyl]amino}propanoic acid | 0.002 | 100 |
| (3S)-3-(1,3-benzodioxol-5-yl)-3-({[(1S)-3-(methylsulfanyl)-1-(phenoxymethyl) propyl]amino}carbonyl)amino]propanoic acid | 20 | 100 |
| (3S)-3-(1,3-benzodioxol-5-yl)-3-{[(methyl{(1S)-3-(methylsulfanyl)-1-[(phenyl sulfanyl)methyl]propyl}amino)carbonyl]amino}propanoic acid | 35 | 78 |
| (3S)-3-(1,3-benzodioxol-5-yl)-3-{[({1-[(phenylsulfanyl)methyl]pentyl}oxy)carbonyl] amino}propanoic acid | 6 | 100 |
| (3S)-3-(1,3-benzodioxol-5-yl)-3-{[({2-(phenylsulfanyl)-1-[(phenylsulfanyl)methyl] ethyl}amino)carbonyl]amino}propanoic acid | 1.5 | 99 |
| (3S)-3-(1,3-benzodioxol-5-yl)-3-{[({(1S)-2-[(carboxymethyl)sulfanyl]-1-[(phenyl sulfanyl)methyl]ethyl}amino)carbonyl]amino}propanoic acid | 2 | 100 |
| (3S)-3-[({[(1S)-1-{[(3-aminophenyl)thio]methyl}-3-(methylthio)propyl]amino} carbonyl)amino]-3-(1,3-benzodioxol-5-yl)propanoic acid | 0.3 | 100 |
| (3S)-3-(1,3-benzodioxol-5-yl)-3-({[(1S)-1-[({4-[(2-methylbenzyl)amino]phenyl}thio) methyl]-3-(methylthio)propyl]amino}carbonyl)amino]propanoic acid | 2 | 93 |
| (3S)-3-(1,3-benzodioxol-5-yl)-3-({[(1S)-1-[({3-[(methylsulfonyl)amino]phenyl}thio) methyl]-3-(methylthio)propyl]amino}carbonyl)amino]propanoic acid | 0.4 | 100 |
| (3S)-3-(1,3-benzodioxol-5-yl)-3-{[({(1S)-3-(methylthio)-1-[({3-[(propyl sulfonyl)amino]phenyl}thio)methyl]propyl}amino)carbonyl]amino}propanoic acid | 0.5 | 100 |
| (3S)-3-{[({(1S)-2-(allyloxy)-1-[(phenylthio)methyl]ethyl}amino)carbonyl]amino}-3-(1,3-benzodioxol-5-yl)propanoic acid | 0.3 | 100 |
| (3S)-3-(1,3-benzodioxol-5-yl)-3-{[({(1S)-2-(benzyloxy)-1-[(phenylthio)methyl]ethyl} amino)carbonyl]amino}propanoic acid | 0.3 | 100 |
| (3S)-3-(1,3-benzodioxol-5-yl)-3-[({[(1R)-1-phenyl-2-(propylthio)ethyl]amino} carbonyl)amino]propanoic acid | 25 | 100 |
| (3S)-3-(1,3-benzodioxol-5-yl)-3-({[(1R)-1-benzyl-2-(propylthio)ethyl]amino} carbonyl)amino]propanoic acid | 2 | 100 |
| (3S)-3-(1,3-benzodioxol-5-yl)-3-{[({(1S)-3-(phenylthio)-1-[(phenylthio)methyl] propyl}amino)carbonyl]amino}propanoic acid | 0.3 | 100 |
| (3S)-3-(1,3-benzodioxol-5-yl)-3-{[({(1S)-4-hydroxy-1-[(phenylthio)methyl]butyl} amino)carbonyl]amino}propanoic acid | 2 | 100 |
| (3S)-3-(1,3-benzodioxol-5-yl)-3-{[({(1S)-2-ethoxy-1-[(phenylthio)methyl]ethyl}oxy) carbonyl]amino}propanoic acid | 5 | 100 |
| (3S)-3-(1,3-benzodioxol-5-yl)-3-{[({(1S)-2-(phenethyloxy)-1-[(phenylthio)methyl] ethyl}oxy)carbonyl]amino}propanoic acid | 4 | 100 |
| (3S)-3-(1,3-benzodioxol-5-yl)-3-{[({(1S)-2-[(cyclopropylmethyl)thio]-1-[(phenylthio) methyl]ethyl}amino)carbonyl]amino}propanoic acid | 0.2 | 100 |
| (3S)-3-(1,3-benzodioxol-5-yl)-3-{[({(1R)-2-(benzyloxy)-1-[(benzylthio)methyl]ethyl} amino)carbonyl]amino}propanoic acid | 1 | 100 |
| (3S)-3-(1,3-benzodioxol-5-yl)-3-{[({(1R)-2-(benzyloxy)-1-[(benzylthio)methyl]ethyl} oxy)carbonyl]amino}propanoic acid | 10 | 100 |
| (3S)-3-(1,3-benzodioxol-5-yl)-3-{[({(1R)-2-(benzyloxy)-1-[(ethylthio)methyl]ethyl} oxy)carbonyl]amino}propanoic acid | 12 | 100 |
| (3S)-3-(1,3-benzodioxol-5-yl)-3-{[({(1S)-2-(ethylthio)-1-[(phenylthio)methyl]ethyl} oxy)carbonyl]amino}propanoic acid | 1 | 100 |

TABLE 1-continued

| Compound | IC$_{50}$ | % A |
|---|---|---|
| (3S)-3-(1,3-benzodioxol-5-yl)-3-{[({(1S)-2-(benzylthio)-1-[(phenylthio)methyl]ethyl}oxy)carbonyl]amino}propanoic acid | 3 | 100 |
| (3S)-3-(1,3-benzodioxol-5-yl)-3-{[({(1S)-1-[({4-[(2-toluidinocarbonyl)amino]phenyl}thio)methyl]pentyl}oxy)carbonyl]amino}propanoic acid | 0.3 | 100 |
| (3S)-3-(1,3-benzodioxol-5-yl)-3-{[({(1S)-1-[({3-[(2-methylbenzyl)amino]phenyl}thio)methyl]pentyl}oxy)carbonyl]amino}propanoic acid, 15 | 25 | 100 |
| (3S)-3-(1,3-benzodioxol-5-yl)-3-{[({(1S)-2-{[(4-methylphenyl)sulfonyl]amino}-1-[(phenylthio)methyl]ethyl}amino)carbonyl]amino}propanoic acid | 10 | 98 |
| (3S)-3-(1,3-benzodioxol-5-yl)-3-{[({(1S)-1-[(2-thienylmethoxy)methyl]pentyl}amino)carbonyl]amino}propanoic acid, 22 | 1.5 | 100 |

TABLE 2

| Compound Number | IC$_{50}$ (nM) |
|---|---|
| 34 | 250 |
| 35 | 350 |
| 36 | 1000 |
| 37 | 30 |
| 38 | 20 |
| 39 | 50 |
| 40 | 120 |
| 41 | 100 |
| 42 | 60 |
| 43 | 120 |

All references cited are hereby incorporated by reference.

The present invention is ellustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims:

We claim:

1. A compound of the structure

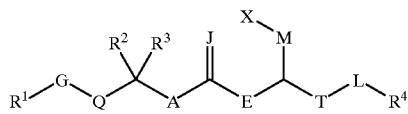

wherein A is selected from the group consisting of —O—, —S—, and —NR$^5$—;

E is selected from the group consisting of —CH$_2$—, —O—, —S—, and —NR$^6$—;

Q is selected from the group consisting of —C(O)— and —(CH$_2$)$_k$— wherein k is an integer of 0 or 1;

J is selected from the group consisting of —O—, —S— and —NR$^8$—;

G is selected from the group consisting of —O—, —NH—, —S—, and —(CH$_2$)$_p$— wherein p is an integer of 0 or 1;

T is selected from the group consisting of —C(O)— and —(CH$_2$)$_b$— wherein b is an integer of from 0 to 3;

L is selected from the group consisting of —O—, —NR$^7$—, —S—, and —(CH$_2$)$_n$— wherein n is an integer of 0 or 1;

B, R$^5$, R$^6$, R$^7$ and R$^8$ are independently selected from the group consisting of hydrogen halogen, hydroxyl, alkyl, alkenyl, alkynyl, alkoxy, alkenoxy, alkynoxy, thioalkoxy, aliphatic acyl, —CF$_3$, nitro, amino, cyano, —N(C$_1$-C$_3$ alkyl)—C(O)(C$_1$-C$_3$ alkyl), —C$_1$-C$_3$ alkylamino, alkenylamino, alkynylamino, di(C$_1$-C$_3$ alkyl)amino, —C(O)O—(C$_1$-C$_3$ alkyl), —C(O)NH—(C$_1$-C$_3$ alkyl), —CH=NOH, —PO$_3$H$_2$, —OPO$_3$H$_2$, —C(O)N(C$_1$-C$_3$ alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkenyl, aralkyl, alkylheterocyclyl, heterocyclylalkyl, sulfonyl, sulfonamido, carbamate, aryloxyalkyl, carboxyl and —C(O)NH(benzyl);

R$^1$, R$^2$ and R$^3$ are independently selected from the group consisting of hydrogen, alkoxy, alkoxyalkoxy, aryl, alkylaryl, arylalkyl, heterocyclyl, alkylheterocyclyl, heterocyclylalkyl and alkyl;

R$^4$ is selected from the group consisting of aryl, alkylaryl, arylalkyl, heterocyclyl, alkylheterocyclyl and heterocyclylalkyl;

X is —CO$_2$B; and

M is —C(R$^9$)(R$^{10}$)— wherein R$^9$ and R$^{10}$ are independently selected from the group consisting of hydrogen and lower alkyl;

wherein B, R$^1$, R$^2$, R$^3$, R$^4$, R$^5$, R$^6$, R$^7$, R$^8$, R$^9$ and R$^{10}$ are unsubstituted or substituted with at least one electron donating or electron withdrawing group;

and wherein R$^2$ and R$^3$ taken together may form a first ring;

R$^4$ and R$^7$ taken together may form a second ring;

R$^9$ and R$^{10}$ taken together may form a third ring;

and pharmaceutically acceptable salts or pro-drugs thereof.

2. A compound of the structure

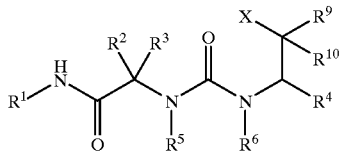

wherein X is selected from the group consisting of —CO$_2$B, —PO$_3$H$_2$, —SO$_3$H, —OPO$_3$H$_2$, —C(O)NHC(O)R$^{11}$, —C(O)NHSO$_2$R$^{12}$, oxazolyl, tetrazolyl and hydrogen; and B, R$^1$, R$^2$, R$^3$, R$^4$, R$^5$, R$^6$, R$^9$, R$^{10}$, R$^{11}$, and R$^{12}$ are independently selected from the group consisting of hydrogen, halogen, hydroxyl, alkyl, alkenyl, alkynyl, alkoxy, alkenoxy, alkynoxy, thioalkoxy, aliphatic acyl, —$CF_3$, nitro, amino, cyano, —$N(C_1-C_3$ alkyl)—C(O) ($C_1-C_3$ alkyl), —$C_1-C_3$ alkylamino, alkenylamino, alkynylamino, di($C_1-C_3$ alkyl)amino, —C(O)O— ($C_1-C_3$ alkyl), —C(O)NH—($C_1-C_3$ alkyl), —CH=NOH, —$PO_3H_2$, —$OPO_3H_2$, —C(O)N($C_1-C_3$ alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkenyl, aralkyl, alkylheterocyclyl, heterocyclylalkyl, sulfonyl, sulfonamido, carbamate, aryloxyalkyl, carboxyl and —C(O)NH(benzyl);

wherein B, $R^1$, $R^2$, $R^3$, $R^4$, $R^5$, $R^6$, $R^9$, $R^{10}$, $R^{11}$ and $R^{12}$ are unsubstituted or substituted with at least one electron donating or electron withdrawing group;

and wherein $R^2$ and $R^3$ taken together may form a first ring;

$R^9$ and $R^{10}$ taken together may form a second ring;

or a pharmaceutically acceptable salt or pro-drug thereof.

3. A compound of claim 2 wherein $R^1$, $R^2$ and $R^3$ are independently selected from the group consisting of hydrogen, alkoxy, alkoxyalkoxy, aryl, alkylaryl, arylalkyl, heterocyclyl, heterocyclylalkyl, alkylheterocyclyl and alkyl;

$R^4$ is selected from the group consisting of aryl, alkylaryl, arylalkyl, heterocyclyl, heterocyclylalkyl and alkyheterocyclyl;

$R^5$ and $R^6$ are hydrogen; and $R^9$ and $R^{10}$ are independently selected from the group consisting of hydrogen and lower alkyl.

4. A compound selected from the group consisting of:

(3S)-3-(1,3-benzodioxol-5-yl)-3-([[((1S)-1-[(2-thienylmethyl)amino]carbonylpentyl)amino]carbonylamino)propanoic acid, (3S)-3-(1,3-benzodioxol-5-yl)-3-([[((1S)-1-[(2-acetylphenyl)amino]carbonylpentyl)amino]carbonylamino)propanoic acid, (3S)-3-(1,3-benzodioxol-5-yl)-3-([[((1S)-1-[(4-acetylphenyl)amino]carbonylpentyl)amino]carbonylamino)propanoic acid, 3-(3S)-3-(1,3-benzodioxol-5-yl)-3-([[((1S)-1-[(4-(2-thienylmethyl)aminobenzyl)amino]carbonylpentyl)amino]carbonylamino)propanoic acid, 3-(3S)-3-(1,3-benzodioxol-5-yl)-3-([[((1S)-1-[(4-(2-methylbenzyloxy)-3-methoxybenzyl)amino]carbonylpentyl)amino]carbonylamino)propanoic acid, 3(3S)-3-(1,3-benzodioxol-5-yl)-3-([[((1S)-1-[(4-(2-methylbenzyl)amino)benzyl)amino]carbonylpentyl)amino]carbonylamino)propanoic acid, 3(3S)-3-(1,3-benzodioxol-5-yl)-3-([[((1S)-1-[(4-(1,3-thiazol-2-ylmethyl)aminobenzyl)amino]carbonylpentyl)amino]carbonylamino)propanoic acid, 3(3S)-3-(1,3-benzodioxol-5-yl)-3-([[((1S)-1-[(4-(5-methyl-2-thienylmethyl)aminobenzyl)amino]carbonylpentyl)amino]carbonylamino)propanoic acid, 3(3S)-3-(1,3-benzodioxol-5-yl)-3-([[((1S)-1-[(4-(2-thienylsulfonamido)benzyl)amino]carbonylpentyl)amino]carbonylamino)propanoic acid, 3(3S)-3-(1,3-benzodioxol-5-yl)-3-([[((1S)-1-[(4-(2-(6-methylpyridyl)methyl)benzyl)amino]carbonylpentyl)amino]carbonylamino)propanoic acid, and pharmaceutically acceptable salts or pro-drugs thereof.

5. A pharmaceutical composition comprising:

a compound of claim 4 in a phannaceutically acceptable carrier.

6. A method for selectively inhibiting $\alpha_4\beta_1$ integrin binding in a mammal comprising administering to said mammal a therapeutic amount of a compound of claim 4.

7. A phannacutical composition comprising:

a compound of claim 2 in a pharmaceutically acceptable carrier.

8. A method for selectively inhibiting $\alpha_4\beta_1$ integrin binding in a mammal comprising administering to said mammal a therapeutic amount of a compound of claim 2.

9. A pharmaceutical composition comprising:

a compound of claim 1 in a pharmaceutically acceptable carrier.

10. A method for selectively inhibiting $\alpha_4\beta_1$ integrin binding in a mammal comprising administering to said mammal a therapeutic amount of a compound of claim 1.

* * * * *

UNITED STATES PATENT AND TRADEMARK OFFICE
CERTIFICATE OF CORRECTION

PATENT NO. : 6,262,084 B1
DATED : July 17, 2001
INVENTOR(S) : Biediger et al.

It is certified that error appears in the above-identified patent and that said Letters Patent is hereby corrected as shown below:

Title page,
ABSTRACT,
Line 4, please delete "compositions thereof;" and insert -- composition comprising such compounds --

Column 1,
Line 3, please delete "U.S. Pat. No. 6,096,973" and insert -- U.S. Pat. No. 6,096,773 --
Line 53, please delete "cosinophils" and insert -- eosinophils --

Column 4,
Line 5, before B, please insert -- wherein --
Line 46, please delete "1,3'" and insert -- 13 --

Column 7,
Line 28, please delete "wherein the terns" and insert -- wherein the terms --

Column 17,
Line 19, please delete "intracisternally" and insert -- intracisternally --
Line 39, please delete "biodegragable" and insert -- biodegradable --

Column 18,
Line 14, please delete "microeneapsule" and insert -- microencapsule --

Column 19,
Line 58, please delete "in vivo" and insert -- *in vivo* --

Column 20,
Line 50, please delete "asthra" and insert -- asthma --

Column 21,
Line 14, please delete "(40 ML)" and insert -- (40 mL) --

Column 27,
Line 43, please delete "strmcture" and insert -- structure --

UNITED STATES PATENT AND TRADEMARK OFFICE
CERTIFICATE OF CORRECTION

PATENT NO. : 6,262,084 B1
DATED : July 17, 2001
INVENTOR(S) : Biediger et al.

It is certified that error appears in the above-identified patent and that said Letters Patent is hereby corrected as shown below:

<u>Column 37,</u>
Line 31, please delete "ellustrated" and insert -- illustrated --

Signed and Sealed this

Seventh Day of May, 2002

Attest:

JAMES E. ROGAN
*Attesting Officer*          *Director of the United States Patent and Trademark Office*